(12) United States Patent
Cowley et al.

(10) Patent No.: US 10,287,252 B2
(45) Date of Patent: May 14, 2019

(54) INHIBITORS OF TRYPTOPHAN-2,3-DIOXYGENASE OR INDOLEAMINE-2,3-DIOXYGENASE

(71) Applicant: IOmet Pharma Ltd., Edinburgh, Midlothian (GB)

(72) Inventors: Phillip M. Cowley, Edinburgh (GB); Alan Wise, Edinburgh (GB); Susan Davis, Dundee (GB); Margaret Huggett, Dundee (GB); Michael Kiczun, Dundee (GB)

(73) Assignee: IOmet Pharma Ltd. (GB)

( * ) Notice: Subject to any disclaimer, the term of this patent is extended or adjusted under 35 U.S.C. 154(b) by 0 days.

(21) Appl. No.: 15/524,148

(22) PCT Filed: Nov. 2, 2015

(86) PCT No.: PCT/EP2015/075471
§ 371 (c)(1),
(2) Date: May 3, 2017

(87) PCT Pub. No.: WO2016/071283
PCT Pub. Date: May 12, 2016

(65) Prior Publication Data
US 2018/0037553 A1 Feb. 8, 2018

(30) Foreign Application Priority Data

Nov. 3, 2014 (GB) .................................. 1419579.6

(51) Int. Cl.
*C07D 237/28* (2006.01)
*A61K 31/472* (2006.01)
(Continued)

(52) U.S. Cl.
CPC .......... *C07D 237/28* (2013.01); *A61K 31/472* (2013.01); *A61K 31/4725* (2013.01);
(Continued)

(58) Field of Classification Search
CPC .................................................. C07D 237/28
See application file for complete search history.

(56) References Cited

U.S. PATENT DOCUMENTS

2010/0331307 A1* 12/2010 Salituro ............... A61K 31/497
514/210.21

FOREIGN PATENT DOCUMENTS

WO WO2007/076055 * 7/2007
WO WO2007076055 7/2007
(Continued)

OTHER PUBLICATIONS

McMahon et al. (2000).*
(Continued)

*Primary Examiner* — Paul V Ward
(74) *Attorney, Agent, or Firm* — Yong Zhao; Catherine D. Fitch

(57) ABSTRACT

Provided is a compound for use in medicine for inhibiting tryptophan-2,3-dioxygenase (TDO) and/or indoleamine-2,3-dioxygenase (IDO), which compound comprises formula (I) wherein $X^1$, $X^2$, and $X^7$, may be the same or different and each is independently selected from C and N; $X^3$, $X^4$, $X^5$, and $X^6$ may be the same or different and each is independently selected from C, N, O and S wherein when $X^3$ is N it has a double bond and wherein when $X^6$ is N it has a double bond; the dotted line is a bond which may be present or absent; $R^1$, $R^2$, $R^3$, $R^4$, $R^5$, $R^6$, and $R^7$ may be present or absent and may be the same or different and each is independently selected from H and a substituted or unsubstituted organic group, provided that at least one of $R^2$, $R^3$, $R^4$ and $R^6$ comprises a group Y; and provided that the number of $R^1$, $R^2$, $R^3$, $R^4$, $R^5$, $R^6$, and $R^7$ groups present is such that the respective valencies of $X^1$, $X^2$, $X^3$, $X^4$, $X^5$, $X^6$, and $X^7$ are maintained; and wherein Y is a group having a formula selected from (II), (III), (IV), (V) wherein L may be present or absent, and may be a substituted or unsubstituted organic linking group, and $R^{31}$ and $R^{32}$ may be the same or different and are selected from H and a substituted or unsubstituted organic group, $X^8$ is selected from C and N, and each $R^{313}$ may be the same or different and is selected from H and a substituted or unsubstituted organic group.

(I)

(II)

(III)

(Continued)

-continued

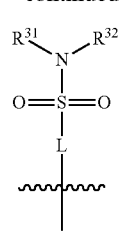
(IV)

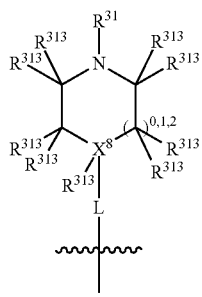

(V)

6 Claims, 2 Drawing Sheets

Figure 1:
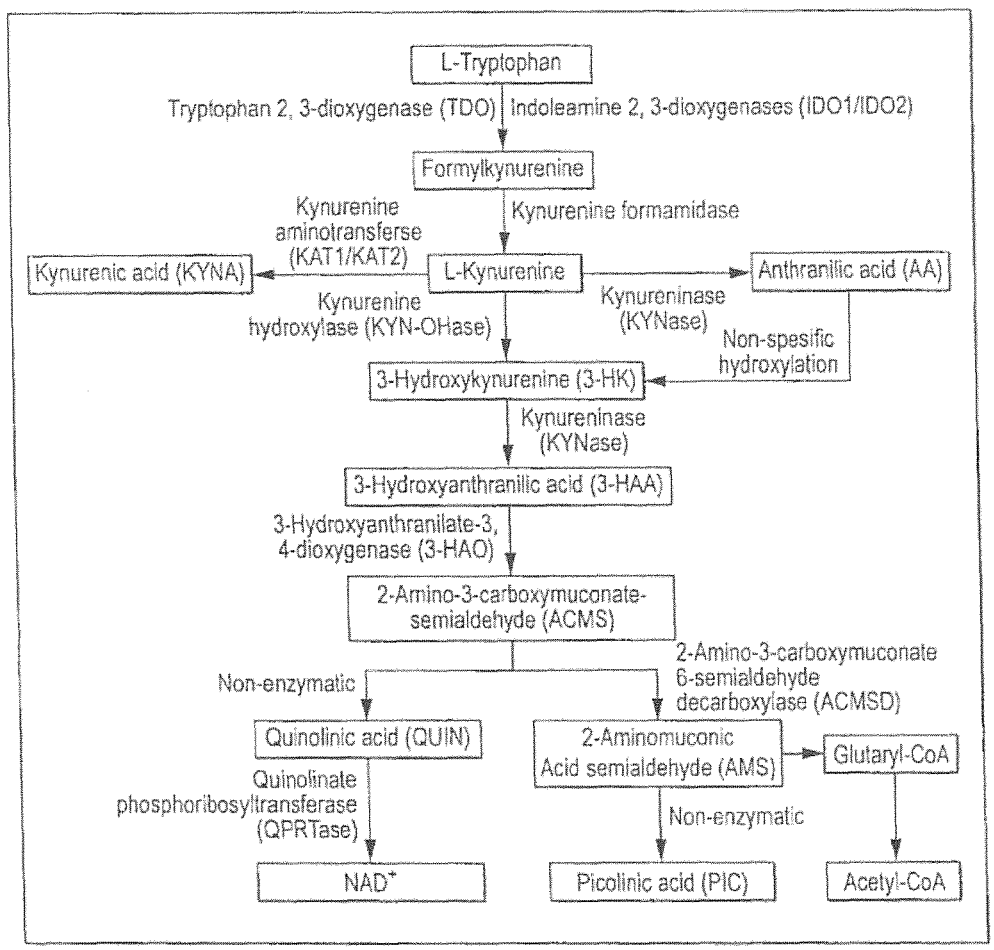

(51) Int. Cl.
| | | |
|---|---|---|
| A61K 31/4725 | (2006.01) | |
| A61K 31/502 | (2006.01) | |
| A61K 45/06 | (2006.01) | |
| C07D 217/02 | (2006.01) | |
| C07D 405/12 | (2006.01) | |
| C07D 409/12 | (2006.01) | |
| C07D 413/12 | (2006.01) | |

(52) U.S. Cl.
CPC ............ *A61K 31/502* (2013.01); *A61K 45/06* (2013.01); *C07D 217/02* (2013.01); *C07D 405/12* (2013.01); *C07D 409/12* (2013.01); *C07D 413/12* (2013.01)

(56) References Cited

FOREIGN PATENT DOCUMENTS

| WO | WO2010092342 | | 8/2010 |
|---|---|---|---|
| WO | WO2012080729 A2 | | 6/2012 |
| WO | WO2012/122534 | * | 9/2012 |
| WO | WO2012122534 | | 9/2012 |
| WO | WO2014141110 | | 9/2014 |
| WO | WO2015031295 | | 3/2015 |
| WO | WO2015150097 | | 10/2015 |

OTHER PUBLICATIONS

Pinedo et al. (2000).*
Galiana-Rosello, In vitro and in vivo antileishmanial and trypanocidal studies of new N-benzene-and N-naphthalenesulfonamide derivatives, Journal of Medicinal Chemistry, 2013, 8984-8998, 56-22.
Kottawar, Shrinivas, S. et al., Synthesis and Antimicrobial Evaluation of Some Heterocyclic Sulfonamide Derivatives, Heteroletters, 2013, p. 31-36, vol. 3, No. 1.
Mansuno, Potent and selective inhibitors of platelet-derived growth factor receptor phosphorylation, J. Med. Chem., 2003, 4910-4925, 46-23.
Rohrig, Rational design of indoleamine 2,3-dioxygenase inhibitors, Journal of Medicinal Chemistry, 2010, 1172-1189, 53.

* cited by examiner

INHIBITORS OF TRYPTOPHAN-2,3-DIOXYGENASE OR INDOLEAMINE-2,3-DIOXYGENASE

CROSS-REFERENCE TO RELATED APPLICATIONS

The present application is a 371 national phase application of international application no. PCT/EP2015/075471, filed Nov. 2, 2015, which claims the benefit of GB Application No. 1419579.6, filed Nov. 3, 2014; hereby incorporated by reference in its entirety.

The present invention relates to tryptophan-2,3-dioxygenase (TDO) or indoleamine-2,3-dioxygenase (IDO [IDO1 or IDO2]) inhibitors, and in particular TDO and IDO inhibitors for use in medicine. The inhibitors of the invention may be used in pharmaceutical compositions, and in particular pharmaceutical compositions for treating a cancer, an inflammatory condition, an infectious disease, a central nervous system disease or disorder and other diseases, conditions and disorders. The invention also relates to methods of manufacture of such inhibitors, and methods of treatment using such inhibitors.

Tryptophan Metabolism

The kynurenine pathway (KP) is responsible for >95% of the degradation of the essential amino acid tryptophan. The kynurenine pathway for tryptophan metabolism leads to the production of the essential pyridine nucleotide NAD+ and a number of neuroactive metabolites, including kynurenine (KYN), kynurenic acid (KYNA), the neurotoxic free-radical generator 3-hydroxykynurenine (3-HK), anthranilic acid, 3-HAA, picolinic acid (PIC), and the excitatory N-methyl-D-aspartate (NMDA) receptor agonist and neurotoxin, quinolinic acid (QUIN) (see FIG. 1). The remaining 5% of tryptophan is metabolised by tryptophan hydroxylase to 5-hydroxytryptophan and then further to 5-hydroxytryptamine (serotonin) and melatonin.

Both the depletion of tryptophan and accumulation of immunosuppressive tryptophan catabolites act to suppress antigen-specific T-cell and natural killer cell responses and induce the formation of regulatory T cells. Because tryptophan catabolism is induced by inflammatory mediators, notably IFN-γ, it is thought to represent an endogenous mechanism that restricts excessive immune responses, thereby preventing immunopathology. However, there is evidence that in disease states this feedback loop may not be beneficial (reviewed in (Munn and Mellor, 2013).

IDO/TDO

The first step of tryptophan catabolism is catalysed by either TDO or IDO. Both enzymes catalyze the oxidative cleavage of the 2,3 double bond in the indole ring, converting tryptophan to N-formylkynurenine. This is the rate-limiting step in tryptophan catabolism by the kynurenine pathway (Grohmann et al., 2003; Stone and Darlington, 2002). TDO is a homotetramer, with each monomer having a molecular mass of 48 kDa, whereas IDO has a molecular mass of 45 kDa and a monomeric structure (Sugimoto et al., 2006; Thackray et al., 2008; Zhang et al., 2007). Despite mediating the same reaction, TDO and IDO are structurally distinct, sharing only 10% homology mainly within the active site (Thackray et al., 2008).

TDO is expressed at high levels in the liver and is responsible for regulating systemic tryptophan levels. TDO is not induced or regulated by signals from the immune system, however TDO expression can be induced by tryptophan or corticosteroids (Miller et al., 2004; Salter and Pogson, 1985). More recently, TDO has been found to be expressed in the brain, where it regulates the production of neuroactive tryptophan metabolites such as kynurenic acid and quinolinic acid (Kauai et al., 2009).

IDO is the predominant tryptophan catabolising enzyme extra hepatically and is found in numerous cells, including macrophages, microglia, neurons and astrocytes (Guillemin et al., 2007; Guillemin et al., 2001; Guillemin et al., 2003; Guillemin et al., 2005). IDO transcription is stringently controlled, responding to specific inflammatory mediators. The mouse and human IDO gene promoters contain multiple sequence elements that confer responsiveness to type I (IFN-α/β) and, more potently, type II (IFN-γ) interferons (Chang et al., 2011; Dai and Gupta, 1990; Hassanain et al., 1993; Mellor et al., 2003). Various cell types, including certain myeloid-lineage cells (monocyte-derived macrophages and DCs), fibroblasts, endothelial cells and some tumour-cell lines, express IDO after exposure to IFN-γ (Burke et al., 1995; Hwu et al., 2000; Mellor et al., 2003; Munn et al., 1999; Varga et al., 1996). However, the control of IDO transcription is complex and cell-type specific. IDO activity is found constitutively at the maternal-fetal interface, expressed by human extravillous trophoblast cells (Kudo and Boyd, 2000). Outside of the placenta, functional IDO expression was reported to be highest in the mouse epididymis, gut (distal ileum and colon), lymph nodes, spleen, thymus and lungs (Takikawa et al., 1986).

Another recent variant enzyme of IDO has been shown to catalyse the same enzymatic step: indoleamine-2,3-dioxygenase 2 (IDO2). However, its physiological relevance remains unclear due to its very low activity, the presence of common polymorphisms that inactivate its enzymatic activity in approximately half of all Caucasians and Asians, and the presence of multiple splice variants (Lob et al., 2008; Meininger et al., 2011; Metz et al., 2007).

IDO-deficient mice are at a gross level phenotypical normal (Mellor et al., 2003), however, they are slightly more prone to induction of autoimmunity and stimulation of the innate immune system. IDO −/− knockout mice also display enhanced inflammatory-mediated colon carcinogenesis and exhibit resistance to inflammation-driven lung and skin cancers (Chang et al., 2011; Yan et al., 2010).

The TDO −/− knockout mouse appears phenotypically normal. However, the TDO knockout mice have a 9-fold increase in the plasma concentration of L-Trp, while IDO −/− knockout mice had WT levels of L-Trp, this suggests that TDO and not IDO regulates systemic Trp. TDO ablation increases Trp in the brain as well as serotonin (5-HT) and is therefore a modulator of anxiety related behaviour (Kanai et al., 2009). TDO also plays a role in the maintenance of brain morphology in adult mice as TDO −/− mice show increased neurogenesis in the hippocampus and subventricular zone during adulthood (Funakoshi et al., 2011).

Immuno-modulation: Tryptophan Depletion and Kynurenine Accumulation

Immunoregulation by tryptophan metabolism modulates the immune system by depletion of the TDO/IDO substrate (tryptophan) in the microenvironment and the accumulation of products such as kynurenine.

Effector T cells are particularly susceptible to low tryptophan concentrations, therefore, depletion of the essential amino acid tryptophan from the local microenvironment resulting in effector T-cell anergy and apoptosis. The depletion of tryptophan is detected by the general control non-derepressible-2 kinase (GCN2) (Munn et al., 2005). The activation of GCN2 triggers a stress-response program that results in cell-cycle arrest, differentiation, adaptation or apoptosis. T cells lacking GCN2 in mice are not susceptible to IDO-mediated anergy by myeloid cells, including dendritic cells in tumor-draining lymph nodes (Munn et al., 2005).

Tryptophan metabolites such as kynurenine, kynurenic acid, 3-hydroxy-kynurenine, and 3-hydroxy-anthranilic acid suppress T-cell function and are capable of inducing T-cell apoptosis. Recent studies have shown that the aryl hydrocarbon receptor (AHR) is a direct target of kynurenine (Mezrich et al., 2010; Nguyen et al., 2010; Opitz et al., 2011). The AHR is a basic helix-loop-helix Per-Arnt-Sim (PAS) family transcription factor. As kynurenine accumulates in a tumour, KYN binds the AHR, translocates to the nucleus and activates transcription of target genes regulated by dioxin-responsive elements (DREs). In T-helper-cells kynurenine results in the generation of regulatory T cells (Treg).

Pharmacological inhibitors of TDO and/or IDO have utility in a wide range of indications, including Infectious diseases, cancer, neurological conditions and many other diseases.

Infectious Diseases and Inflammation

Infection by bacteria, parasites, or viruses induces a strong IFN-γ-dependent inflammatory response. IDO can dampen protective host immunity, thus indirectly leading to increased pathogen burdens. For example, IDO activity attenuates *Toxoplasma gondii* replication in the lung, and the inflammatory damage is significantly decreased by the administration of the IDO inhibitor 1MT after infection (Murakami et al., 2012). Also, in mice infected with murine leukaemia virus (MuLV), IDO was found to be highly expressed, and ablation of IDO enhanced control of viral replication and increased survival (Hoshi et al., 2010). In a model of influenza infection, the immunosuppressive effects of IDO could predispose lungs to secondary bacterial infection (van der Sluijs., et al 2006). In Chagas Disease, which is caused by the *Trypanosoma cruzi* parasite, kynurenine is increased in patients and correlates with disease severity (Maranon et al., 2013). Therefore, IDO inhibitors could be used to improve the outcomes of patients with a wide variety of infectious diseases and inflammatory conditions. Given the role of TDO in controlling systemic Trp levels, TDO inhibitors could also be used to improve the outcomes of patients with a wide variety of infectious diseases and inflammatory conditions.

IDO and Immunity to Gut Bacteria

IDO plays a role in regulating mucosal immunity to the intestinal microbiota. IDO has been shown to regulate commensal induced antibody production in the gut; IDO-deficient mice had elevated baseline levels of immunoglobulin A (IgA) and immunoglobulin G (IgG) in the serum and increased IgA in intestinal secretions. Due to elevated antibody production, IDO deficient mice were more resistant to intestinal colonization by the gram-negative enteric bacterial pathogen *Citrobacter rodentium* than WT mice. IDO-deficient mice also displayed enhanced resistance to the colitis caused by infection with *C. rodentium* (Harrington et al., 2008).

Therefore, pharmacological targeting of IDO activity may represent a new approach to manipulating intestinal immunity and controlling the pathology caused by enteric pathogens including colitis (Harrington et al., 2008).

HIV Infection

Patients infected with HIV have chronically reduced levels of plasma tryptophan and increased levels of kynurenine, and increased IDO expression (Fuchs et al., 1990 and Zangerle et al., 2002).

In HIV patients the upregulation of IDO acts to suppress immune responses to HIV antigens contributing to the immune evasion of the virus. HIV triggers high levels of IDO expression when it infects human macrophages in vitro (Grant et al., 2000), and simian immunodeficiency virus (SIV) infection of the brain in vivo induces IDO expression by cells of the macrophage lineage (Burudi et al., 2002).

The pathogenesis of HIV is characterized by CD4+ T cell depletion and chronic T cell activation, leading ultimately to AIDS (Douek et al., 2009). CD4+ T helper (TH) cells provide protective immunity and immune regulation through different immune cell functional subsets, including TH1, TH2, T regulatory (Treg), and TH17 cells. Progressive HIV is associated with the loss of TH17 cells and a reciprocal increase in the fraction of the immunosuppressive Treg cells. The loss of TH17/Treg balance is associated with induction of IDO by myeloid antigen-presenting dendritic cells (Favre et al., 2010). In vitro, the loss of TH17/Treg balance is mediated directly by the proximal tryptophan catabolite from IDO metabolism, 3-hydroxyanthranilic acid. Therefore in progressive HIV, induction of IDO contributes to the inversion of the TH17/Treg balance and maintenance of a chronic inflammatory state (Favre et al., 2010). Therefore, IDO inhibitors could have utility in addressing the TH17/Treg balance in HIV.

Sepsis-induced Hypotension

Systemic inflammation such as sepsis is characterized by arterial hypotension and systemic inflammatory response syndrome (Riedemann et al., 2003). The associated increase in circulating pro-inflammatory cytokines, including interferon-γ (IFN-γ), leads to the unchecked production of effector molecules such as reactive oxygen and nitrogen species that themselves can contribute to pathology (Riedemann et al., 2003).

The metabolism of tryptophan to kynurenine by IDO expressed in endothelial cells contributes to arterial vessel relaxation and the control of blood pressure (Wang et al., 2010). Infection of mice with malarial parasites (*Plasmodium berghei*), and experimental induction of endotoxemia, caused endothelial expression of IDO, resulting in decreased plasma tryptophan, increased kynurenine, and hypotension. Pharmacological inhibition of IDO increased blood pressure in systemically inflamed mice, but not in mice deficient for IDO or interferon-γ, which is required for IDO induction. Arterial relaxation by kynurenine was mediated by activation of the adenylate and soluble guanylate cyclase pathways. (Wang et al., 2010). Therefore, inhibitors of IDO (and TDO, given its role in controlling systemic Trp levels) could have utility in treating sepsis-induced hypotension.

CNS Disorders

In the central nervous system both fates of TRP which act as a precursor to kynurenine and serotonin are pathways of interest and importance. Metabolites produced by the kynurenine pathway have been implicated to play a role in the pathomechanism of neuroinflammatory and neurodegenerative disorder (summarised in FIG. 2). The first stable intermediate from the kynurenine pathway is KYN. Subsequently, several neuroactive intermediates are generated. They include kynurenic acid (KYNA), 3-hydroxykynurenine (3-HK), and quinolinic acid (QUIN). 3-HK and QUIN are neurotoxic by distinct mechanisms; 3-HK is a potent free-radical generator (Hiraku et al., 1995; Ishii et al., 1992; Thevandavakkam et al., 2010), whereas QUIN is an excitotoxic N-methyl-D-aspartate (NMDA) receptor agonist (Schwarcz et al., 1983; Stone and Perkins, 1981). KYNA, on the other hand, has neuroprotective properties as an antagonist of excitatory amino acid receptors and a free-radical scavenger (Carpenedo et al., 2001; Foster et al., 1984; Goda et al., 1999; Vecsei and Beal, 1990). Changes in the concentration levels of kynurenines can shift the balance to pathological conditions. The ability to influence the metabolism towards the neuroprotective branch of the kynurenine pathway, i.e. towards kynurenic acid (KYNA) synthesis, may be one option in preventing neurodegenerative diseases.

In the CNS, the kynurenine pathway is present to varying extents in most cell types, Infiltrating macrophages, activated microglia and neurons have the complete repertoire of kynurenine pathway enzymes. On the other hand, neuroprotective astrocytes and oligodendrocytes lack the enzyme, kynurenine 3-monooxygenase (KMO) and IDO-1 respectively, and are incapable of synthesizing the excitotoxin, quinolinic acid (QUIN) (Guillemin et al., 2000; Lim et al., 2007). TDO is expressed in low quantities in the brain, and is induced by TRP or corticosteroids (Salter and Pogson 1985; Miller et al., 2004).

Given the role of TDO and IDO in the pathogenesis of several CNS disorders as well as the role of TDO in controlling systemic Trp levels, IDO and/or TDO inhibitors could be used to improve the outcomes of patients with a wide variety of CNS diseases and neurodegeneration.

Amyotrophic Lateral Sclerosis

Amyotrophic lateral sclerosis (ALS), or Lou Gehrig's disease, is a progressive and fatal neurodegenerative disease targeting the motor system. ALS results in the selective attacking and destruction of motor neurons in the motor cortex, brainstem and spinal cord.

Although multiple mechanisms are likely to contribute to ALS, the kynurenine pathway activated during neuroinflammation is emerging as a contributing factor. Initial inflammation may inflict a nonlethal injury to motor neurons of individuals with a susceptible genetic constitution, in turn triggering a progressive inflammatory process which activates microglia to produce neurotoxic kynurenine metabolites that further destroy motor neurons.

In the brain and spinal cord of ALS patients large numbers of activated microglia, reactive astrocytes, T cells and infiltrating macrophages have been observed (Graves et al., 2004; Henkel et al., 2004). These cells release inflammatory and neurotoxic mediators, among others IFN-γ, the most potent inducer of IDO (McGeer and McGeer 2002). The neuronal and microglial expression of IDO is increased in ALS motor cortex and spinal cord (Chen et al., 2010). It has been proposed that the release of immune activating agents activates the rate-limiting enzyme of the KP, IDO, which generates metabolites such as the neurotoxin QUIN. Therefore, inhibition of IDO would reduce the synthesis of neurotoxic QUIN, which has been clearly implicated in the pathogenesis of ALS.

Huntington's Disease

Huntington's disease (HD) is a genetic autosomal dominant neurodegenerative disorder caused by expansion of the CAG repeats in the huntingtin (htt) gene. Patients affected by HD display progressive motor dysfunctions characterized by abnormality of voluntary and involuntary movements (choreoathetosis) and psychiatric and cognitive disturbances. In-life monitoring of metabolites within the KYN pathway provide one of the few biomarkers that correlates with the number of CAG repeats and hence the severity of the disorder (Forrest et al., 2010). Post mortem very high levels of QUIN are found located in areas of neurodegeneration, while striatal glutamatergic neurones, on which QUIN acts as an excitotoxin, are a principal class lost in the disease. Importantly, TDO ablation in a *Drosophila* model of Huntington's disease ameliorated neurodegeneration (Campesan et al., 2011).

Alzheimer's Disease

Alzheimer's disease (AD) is an age-related neurodegenerative disorder characterised by neuronal loss and dementia. The histopathology of the disease is manifested by the accumulation of intracellular β-amyloid (Aβ) and subsequent formation of neuritic plaques as well as the presence of neurofibrillary tangles in specific brain regions associated with learning and memory. The pathological mechanisms underlying this disease are still controversial, however, there is growing evidence implicating KP metabolites in the development and progression of AD.

It has been shown that Aβ (1-42) can activate primary cultured microglia and induce IDO expression (Guillemin et al., 2003; Walker et al., 2006). Furthermore, IDO overexpression and increased production of QUIN have been observed in microglia associated with the amyloid plaques in the brain of AD patients (Guillemin et al., 2005). QUIN has been shown to lead to tau hyperphosphorylation in human cortical neurons (Rahman et al., 2009). Thus, overexpression of IDO and over-activation of the KP in microglia are implicated in the pathogenesis of AD.

There is also evidence for TDO involvement in Alzheimer's disease. TDO is upregulated in the brain of patients and AD mice models. Furthermore, TDO co-localizes with quinolinic acid, neurofibrillary tangles-tau and amyloid deposits in the hippocampus of AD patients (Wu et al., 2013). Therefore, the kynurenine pathway is over-activated in AD by both TDO and IDO and may be involved in neurofibrillary tangle formation and associated with senile plaque formation.

Psychiatric Disorders and Pain

Most tryptophan is processed through the kynurenine pathway. A small proportion of tryptophan is processed to 5-HT and hence to melatonin, both of which are also substrates for IDO. It has long been known that amongst other effects acute tryptophan depletion can trigger a depressive episode and produces a profound change in mood even in healthy individuals. These observations link well with the clinical benefits of serotonergic drugs both to enhance mood and stimulate neurogenesis.

The co-morbidity of depressive symptoms, implication of the kynurenine pathway in inflammation and an emerging link between TDO and the glucocorticoid mediated stress response also implicate a role in the treatment of chronic pain (Stone and Darlington 2013).

Schizophrenic patients exhibit elevated KYN levels both in CSF and brain tissue, particularly the frontal cortex. This has been associated with the "hypofrontality" observed in schizophrenia. Indeed rodents treated with neuroleptics show a marked reduction in frontal KYN levels. These changes have been associated with reduced KMO and 3HAO. Evidence includes an association between a KMO polymorphism, elevated CSF KYN and schizophrenia (Holtze etr al., 2012). Taken together there is potential for manipulations in this pathway to be both pro-cognate and neuroleptic.

Pain and depression are frequently comorbid disorders. It has been shown that IDO plays a key role in this comorbidity. Recent studies have shown that IDO activity is linked to (a) decreased serotonin content and depression (Dantzer et al., 2008; Sullivan et al., 1992) and (b) increased kynurenine content and neuroplastic changes through the effect of its derivatives such as quinolinic acid on glutamate receptors (Heyes et al., 1992).

In rats chronic pain induced depressive behaviour and IDO upregulation in the bilateral hippocampus. Upregulation of IDO resulted in the increased kynurenine/tryptophan ratio and decreased serotonin/tryptophan ratio in the bilateral hippocampus. Furthermore, IDO gene knockout or pharmacological inhibition of hippocampal IDO activity attenuated both nociceptive and depressive behaviour (Kim et al., 2012).

Since proinflammatory cytokines have been implicated in the pathophysiology of both pain and depression, the regulation of brain IDO by proinflammatory cytokines serves as a critical mechanistic link in the comorbid relationship between pain and depression through the regulation of tryptophan metabolism.

Multiple Sclerosis

Multiple sclerosis (MS) is an autoimmune disease characterized by inflammatory lesions in the white matter of the nervous system, consisting of a specific immune response to the myelin sheet resulting in inflammation and axonal loss (Trapp et al., 1999; Owens, 2003).

Accumulation of neurotoxic kynurenine metabolites caused by the activation of the immune system is implicated in the pathogenesis of MS. QUIN was found to be selectively elevated in the spinal cords of rats with EAE, an autoimmune animal model of MS (Flanagan et al., 1995). The origin of the increased QUIN in EAE was suggested to be the macrophages. QUIN is an initiator of lipid peroxidation and high local levels of QUIN near myelin may contribute to the demyelination in EAE and possibly MS.

Interferon beta 1b (IFN-β1b) induces KP metabolism in macrophages at concentrations comparable to those found in the sera of IFN-b treated patients, this which may be a limiting factor in its efficacy in the treatment of MS (Guillemin et al., 2001). After IFN-β administration, increased kynurenine levels and kynurenine/tryptophan ratio were found in the plasma of MS patients receiving IFN-b injection compared to healthy subjects indicating an induction of IDO by IFN-β (Amirkhani et al., 2005). IFN-β1b, leads to production of QUIN at concentrations sufficient to disturb the ability of neuronal dendrites to integrate incoming signals and kill oligodendrocytes (Cammer 2001). In IFN-β1b-treated patients concomitant blockade of the KP with an IDO/TDO inhibitor may improve its efficacy of IFN-β1b.

Parkinson's Disease

Parkinson's disease (PD) is a common neurodegenerative disorder characterised by loss of dopaminergic neurons and localized neuroinflammation.

Parkinson's disease is associated with chronic activation of microglia (Gao and Hong, 2008). Microglia activation release neurotoxic substances including reactive oxygen species (ROS) and proinflammatory cytokines such as INF-γ (Block et al., 2007), a potent activator of KP via induction of IDO expression. KP in activated microglia leads to upregulation of 3HK and QUIN. 3HK is toxic primarily as a result of conversion to ROS (Okuda et al., 1998). The combined effects of ROS and NMDA receptor-mediated excitotoxicity by QUIN contribute to the dysfunction of neurons and their death (Braidy et al., 2009; Stone and Perkins, 1981). However, picolinic acid (PIC) produced through KP activation in neurons, has the ability to protect neurons against QUIN-induced neurotoxicity, being NMDA agonist (Jhamandas et al., 1990). Microglia can become overactivated, by proinflammatory mediators and stimuli from dying neurons and cause perpetuating cycle of further microglia activation microgliosis. Excessive microgliosis will cause neurotoxicity to neighbouring neurons and resulting in neuronal death, contributing to progression of Parkinson's disease. (Zinger et al 2011): Therefore, PD is associated with an imbalance between the two main branches of the KP within the brain. KYNA synthesis by astrocytes is decreased and concomitantly, QUIN production by microglia is increased.

HIV

HIV patients, particularly those with HIV-linked dementia (Kandanearatchi & Brew 2012), often have significantly elevated KYN levels in CSF. These levels are directly related to the development of neurocognitive decline and often the presence of sever psychotic symptoms (Stone & Darlington 2013).

Cancer

It is clear that tumours can induce tolerance to their own antigens. Tryptophan catabolism in cancer is increasingly being recognized as an important micro-environmental factor that suppresses antitumor immune responses. Depletion of tryptophan and accumulation of immunosuppressive tryptophan catabolites such as kynurenine create an immunosuppressive milieu in tumours and in tumour-draining lymph nodes by inducing T-cell anergy and apoptosis. Such immunosuppression in the tumour microenvironment may help cancers evade the immune response and enhance tumorigenicity (reviewed in Adam et al., 2012).

Recently, both TDO and IDO have been implicated in tumour progression. Individually TDO or IDO have been found to be overexpressed in various cancers, furthermore, several cancers overexpress both TDO and IDO. TDO and IDO mediate immunosuppressive effects through the metabolization of Trp to kynurenine, triggering downstream signalling through GCN2, mTOR and AHR that can affect differentiation and proliferation of T cells. Also, expression of IDO by activated dendritic cells can serve to activate regulatory T cells (Tregs) and inhibit tumor-specific effector CD8+ T cells, thereby constituting a mechanism by which the immune system can restrict excessive lymphocyte reactivity (reviewed in Platten et al., 2012).

IDO

Increased expression of IDO has been shown to be an independent prognostic variable for reduced survival in patients with acute myeloid leukemia (AML), small-cell lung, melanoma, ovarian, colorectal, pancreatic, and endometrial cancers (Okamoto et al., 2005; Ino et al., 2006). Indeed, sera from cancer patients have higher kynurenine/tryptophan ratios than sera from normal volunteers (Liu et al., 2010; Weinlich et al., 2007; Huang et al., 2002). The level of IDO expression was also shown to correlate with the number of tumour infiltrating lymphocytes in colorectal carcinoma patients (Brandacher et al., 2006).

In preclinical models, transfection of immunogenic tumour cells with recombinant IDO prevented their rejection in mice (Uyttenhove et al., 2003). While, ablation of IDO expression led to a decrease in the incidence and growth of 7,12-dimethylbenz(a)anthracene-induced premalignant skin papillomas (Muller et al., 2008). Moreover, IDO inhibition slows tumour growth and restores anti-tumour immunity (Koblish et al., 2010) and IDO inhibition synergises with cytotoxic agents, vaccines and cytokines to induce potent anti-tumour activity (Uyttenhove et al., 2003; Muller et al., 2005; Zeng et al., 2009).

TDO

TDO is predominantly expressed in the liver and is believed to regulate systemic Trp concentrations, however, TDO was found to be frequently activated and constitutively expressed in glioma cells. TDO derived KYN was shown to suppress antitumor immune responses and promote tumor-cell survival and motility through the AhR in an autocrine manner (Opitz et al., 2011). It was also shown that TDO is elevated in human hepatocellular carcinomas and detected sporadically in other cancers. In a preclinical model, TDO expression prevented rejection of tumor grafts by preimmunized mice. Systemic administration of the TDO inhibitor, LM10, restored the ability of mice to reject TDO-expressing tumors (Pilotte et al., 2012).

Therefore inhibitors of TDO or IDO could have wide ranging therapeutic efficacy in the treatment of cancer. Also dual inhibitors blocking both TDO and IDO may demonstrate improved clinical efficacy by targeting both of these key Trp-metabolising enzymes and would also treat a wider patient population: in a series of 104 human tumor lines of various histological types, 20 tumors expressed only TDO, 17 expressing only IDO and 16 expressed both. Therefore, targeting both IDO and TDO would allow reaching 51% of tumors instead of 32% with IDO or 35% with TDO alone (Pilotte et al., 2012). Moreover, given the role of TDO in controlling systemic Trp levels, TDO inhibitors could also be used to improve the outcomes of patients with a wide variety of cancers and neoplastic diseases that do not express TDO.

Inhibition of IDO and/or TDO will dramatically lower kynurenine levels, relieving the brake on the immune system allowing it to attack and eliminate tumours. While there is evidence that a TDO/IDO inhibitor would be useful as a stand-alone agent, inhibitors of this type would be particularly effective when used in combination with other cancer immunotherapies. In fact, upregulation of IDO expression has been identified as a mechanism by which tumours gain resistance to the CTLA-4 blocking antibody ipilimumab. Ipilimumab blocks the co-stimulatory molecule CTLA-4, causing tumour-specific T cells to remain in an activated state. IDO knockout mice treated with anti-CTLA-4 antibody demonstrate a striking delay in B16 melanoma tumor growth and increased overall survival when compared with wild-type mice. Also, CTLA-4 blockade strongly synergizes with IDO inhibitors to mediate tumour rejection. Similar data was also reported for IDO inhibitors in combination with anti-PD1 and anti-PDL-1 antibodies (Holmgaard et al., 2013).

Agents that will influence an immunosuppressive environment may also be relevant to chimeric antigen receptor T cell therapy (CAR-T) therapies to enhance efficacy and patient responses.

Other Diseases

Although these effects are defensive strategies to cope with infection and inflammation, they may have unintended consequences because kynurenines formed during IDO and TDO-mediated degradation of tryptophan can chemically modify proteins and have been shown to be cytotoxic (Morita et al., 2001; Okuda et al., 1998). In coronary heart disease, inflammation and immune activation are associated with increased blood levels of kynurenine (Wirleitner et al., 2003) possibly via interferon-γ-mediated activation of IDO. In experimental chronic renal failure, activation of IDO leads to increased blood levels of kynurenines (Tankiewicz et al., 2003), and in uremic patients kynurenine-modified proteins are present in urine (Sala et al., 2004). Further, renal IDO expression may be deleterious during inflammation, because it enhances tubular cell injury.

General anaesthesia unfortunately mimics many of these effects inducing stress and inflammatory processes. Post anaesthesia cognitive dysfunction has often been correlated with these sequelae. Recently these deficits have been shown to be correlated with changes in kynurenine pathway markers, but not cytokines, following cardiac surgery and in recovering stroke patients (Stone and Darlington 2013).

Cataracts

A cataract is a clouding of the lens inside the eye that leads to a decrease in vision. Recent studies suggest that kynurenines might chemically alter protein structure in the human lens leading to cataract formation. In the human lens IDO activity is present mainly in the anterior epithelium (Takikawa et al., 1999). Several kynurenines, such as kynurenine (KYN), 3-hydroxykynurenine (3OHKYN), and 3-hydroxykynurenine glucoside (3OHKG) have been detected in the lens; where they were thought to protect the retina by absorbing UV light and therefore are commonly referred to as UV filters. However, several recent studies show that kynurenines are prone to deamination and oxidation to form α,β-unsaturated ketones that chemically react and modify lens proteins (Taylor et al., 2002). Kynurenine mediated modification could contribute to the lens protein modifications during aging and cataractogenesis. They may also reduce the chaperone function of α-crystallin, which is necessary for maintaining lens transparency.

Transgenic mouse lines that overexpress human IDO in the lens developed bilateral cataracts within 3 months of birth. It was demonstrated that IDO-mediated production of kynurenines results in defects in fibre cell differentiation and their apoptosis (Mailankot et al., 2009). Therefore inhibition of IDO may slow the progression of cataract formation.

Female Reproductive Health

Endometriosis

Endometriosis, the presence of endometrium outside the uterine cavity, is a common gynaecological disorder, causing abdominal pain, dyspareunia and infertility. IDO expression was found to be higher in eutopic endometrium from women with endometriosis by microarray analysis (Burney et al., 2007 and Aghajanova et al., 2011). Furthermore, IDO was shown to enhance the survival and invasiveness of endometrial stromal cells (Mei et al., 2013). Therefore, an IDO/TDO inhibitor could be used as a treatment for endometriosis.

Contraception and Abortion

The process of implantation of an embryo requires mechanisms that prevent allograft rejection; and tolerance to the fetal allograft represents an important mechanism for maintaining a pregnancy. Cells expressing IDO in the foetomaternal interface protect the allogeneic foetus from lethal rejection by maternal immune responses. Inhibition of IDO by exposure of pregnant mice to 1-methyl-tryptophan induced a T cell-mediated rejection of allogeneic concepti, whereas syngeneic concepti were not affected; this suggests that IDO expression at the foetal maternal interface is necessary to prevent rejection of the foetal allograft (Munn et al., 1998). Accumulating evidence indicates that IDO production and normal function at the foetal maternal interface may play a prominent role in pregnancy tolerance (Dun and Kindler., 2013). Therefore, an IDO/TDO inhibitor could be used as a contraceptive or abortive agent.

In the Journal of Medicinal Chemistry, Vol. 56 (22), 2013, pp 8984-8998, Galiana-Rosello et al., disclose antileishmanial and trypanocidal compounds. Some compounds are similar to those of the present invention, but TDO and IDO inhibitory activity is not disclosed.

In published patent application EP 1258252 (Eisai) integrin expression inhibitors are disclosed, which may be used for treating a wide range of diseases, one of which is cancer. A wide general formula is disclosed, but none of the specific compounds disclosed are similar to the compounds of the present invention and TDO and IDO inhibitory activity is not disclosed.

In published patent application WO 2012/122534 (Univ. Columbia) compounds for the treatment of cancer, autoimmune disorders and inflammation are disclosed. These compounds differ from the present compounds, and compounds similar to the present compounds were used as references and shown not to be active (compound 85, FIG. 8I). The document furthermore does not disclose TDO and IDO inhibitory activity.

In published patent application WO 2012/080729 (Electrophoretics) casein kinase inhibitors are disclosed for the treatment of neurodegenerative diseases such as Alzheimer's disease. A wide general formula is disclosed. Some compounds are similar to those of the present invention, but TDO and IDO inhibitory activity is not disclosed.

In published patent application WO 2004/101544 (Warner Lambert) androgen receptor agonists are disclosed for treating conditions associated with inappropriate activation of the androgen receptor. This may include, inter alia, cancer. A wide general formula is disclosed, but only one of the specific compounds disclosed is similar to the compounds of the present invention, and the core structure of the compounds is quite different. In particular, TDO and IDO inhibitory activity is not disclosed and the most similar compound (compound 31) is not disclosed to be an active TDO or IDO inhibitor.

In Heterocyclic Letters Vol. 3 (1), 2013, pp 31-36, Kottawar et al., disclose antimicrobial compounds. Some compounds are similar to those of the present invention, but TDO and IDO inhibitory activity is not disclosed.

On the above basis, the inventors have determined that a strong rationale exists for the therapeutic utility of drugs which block the activity of TDO and or IDO, in treating the above-mentioned diseases, conditions and disorders.

Having regard to the above, it is an aim of the present invention to provide TDO or IDO inhibitors, and in particular TDO and IDO inhibitors for use in medicine. It is thus an aim to provide a compound for use in medicine for inhibiting tryptophan-2,3-dioxygenase (TDO) and/or indoleamine-2,3-dioxygenase (IDO). It is a further aim to provide pharmaceutical compositions comprising such inhibitors, and in particular to provide compounds and pharmaceutical compositions for treating a cancer, an inflammatory condition, an infectious disease, a central nervous system disease or disorder and other diseases, conditions and disorders. It is also an aim to provide compounds methods of synthesis of the compounds.

Accordingly, the present invention provides a compound for use in medicine for inhibiting tryptophan-2,3-dioxygenase (TDO) and/or indoleamine-2,3-dioxygenase (IDO), which compound comprises the following formula:

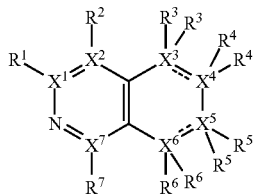

wherein $X^1$, $X^2$, and $X^7$, may be the same or different and each is independently selected from C and N; $X^3$, $X^4$, $X^5$, and $X^6$ may be the same or different and each is independently selected from C, N, O and S wherein when $X^3$ is N it has a double bond and wherein when $X^6$ is N it has a double bond; the dotted line is a bond which may be present or absent; $R^1$, $R^2$, $R^3$, $R^4$, $R^5$, $R^6$, and $R^7$ may be present or absent and may be the same or different and each is independently selected from H and a substituted or unsubstituted organic group, provided that at least one of $R^2$, $R^3$, $R^4$ and $R^6$ comprises a group Y; and provided that the number of $R^1$, $R^2$, $R^3$, $R^4$, $R^5$, $R^6$, and $R^7$ groups present is such that the respective valencies of $X^1$, $X^2$, $X^3$, $X^4$, $X^5$, and $X^7$ are maintained; and wherein Y is a group having a formula selected from the following:

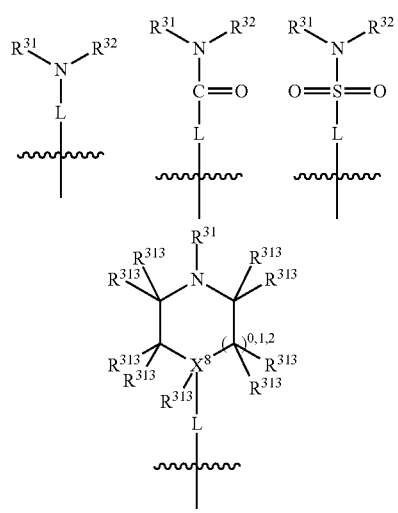

wherein L may be present or absent, and may be a substituted or unsubstituted organic linking group, and $R^{31}$ and $R^{32}$ may be the same or different and are selected from H and a substituted or unsubstituted organic group, $X^8$ is selected from C and N, and each $R^{313}$ may be the same or different and is selected from H and a substituted or unsubstituted organic group.

In the present context the dotted line between two atoms indicates the possible presence of a further bond. In a case where two atoms are already joined by a solid line, but also have a dotted line, then those atoms have at least a single bond, but possibly a double bond in some cases. Thus, in such cases, each atom having a dotted line may independently have a double bond or a single bond, provided that valencies at each atom are maintained. In cases where there is only a dotted line joining two atoms, then these atoms may not be directly bonded at all in some cases, or in other cases may be joined by a single bond.

In the present context the part of the structure present in brackets may be repeated the number of times given by the numbers next to the brackets (whether regular brackets or square brackets). For example, in the case of $(C(R))_{0,1,2}$ or $[C(R)]_{0,1,2}$ the C—R group may be absent, present once i.e. —C(R)—; or present twice i.e. —C(R)—C(R)—.

In the formulae herein, all tautomeric forms of the ring system (including the tautomeric forms of each of the 6-membered rings) are intended to be included.

Throughout this disclosure, any of the compounds disclosed may typically be suitable for use in medicine in a treatment of diseases, especially cancer, which treatment may be effected by tryptophan-2,3-dioxygenase (TDO) and/or indoleamine-2,3-dioxygenase (IDO) inhibition.

In the context of the present invention, maintaining the valency means ensuring that an atom has its normal (typically most common) valency in organic compounds (i.e. 2 for oxygen and sulphur, 3 for nitrogen and 4 for carbon). Nitrogen atoms may, in some instances, have 4 bonds, but in such cases they are typically positively charged such that the compound may have a counter-ion. Such compounds are also considered to be part of the invention, and in these cases, due to the positive charge, it will be clear that the nitrogen atom still maintains its normal valency of 3. For the avoidance of doubt, where the number of R groups may vary according to the choice of X group, it may vary as follows.

$R^1$ is absent when $X^1$ is N and one $R^1$ is present when $X^1$ is C. $R^2$ is absent when $X^2$ is N and one $R^2$ is present when $X^2$ is C. $R^3$ is absent when $X^3$ is N (since when $X^3$ is N it must have a double bond to a ring atom), and when $X^3$ is O or S; one $R^3$ is present when $X^3$ is C and has a double bond; and two $R^3$ are present when $X^3$ is C and has a single bond to each ring atom. $R^4$ is absent when $X^4$ is N and has a double bond to a ring atom, and when $X^4$ is O or S; one $R^4$ is present when $X^4$ is C and has a double bond to a ring atom, and when $X^4$ is N and has two single bonds to each ring atom; and two $R^4$ are present when $X^4$ is C and has a single bond to each ring atom. $R^5$ is absent when $X^5$ is N and has a double bond to a ring atom, and when $X^5$ is O or S; one $R^5$ is present when $X^5$ is C and has a double bond to a ring atom, and when $X^5$ is N and has two single bonds to each ring atom; and two $R^5$ are present when $X^5$ is C and has a single bond to each ring atom. $R^6$ is absent when $X^6$ is N (since when $X^6$ is N it must have a double bond), and when $X^6$ is O or S; one $R^6$ is present when $X^6$ is C and has a double bond to a ring atom; and two $R^6$ are present when $X^6$ is C and has a single bond to each ring atom. $R^7$ is absent when $X^7$ is N and one $R^7$ is present when $X^7$ is C. $R^{313}$ is absent when $X^8$ is N and one $R^{313}$ is present when $X^8$ is C.

In the present context the invention includes compounds in which a single $R^3$, $R^4$, $R^5$, $R^6$, and/or $R^{313}$ group on an atom, or two $R^3$, $R^4$, $R^5$, $R^6$, and/or $R^{313}$ groups on the same atom, may form a group which is double bonded to that atom. Accordingly, an $R^3$, $R^4$, $R^5$, $R^6$, and/or $R^{313}$ group, or two $R^3$, $R^4$, $R^5$, $R^6$, and/or $R^{313}$ groups attached to the same atom, may together form a =O group, or a =C(R')$_2$ group (wherein each R' group is the same or different and is H or an organic group, preferably H or a straight or branched substituted or unsubstituted $C_1$-$C_6$ alkyl group). Typically, all $R^{313}$ groups are H, or one or more of the $R^{313}$ groups adjacent to the N—$R^{31}$, and/or adjacent to the $X^8$, are not H. In some instances two $R^{313}$ groups on the same atom adjacent to the N—$R^{31}$, and/or adjacent to the $X^8$, are not H, and in other instances one $R^{313}$ group on each of the two different atoms adjacent to the N—$R^{31}$, and/or adjacent to the $X^8$, is not H. Typically, the one or more of the $R^{313}$ groups adjacent to the N—$R^{31}$, and/or adjacent to the $X^8$, are selected from a $C_1$-$C_6$ alkyl group. In some instances two $R^3$, $R^4$, $R^5$, $R^6$, and/or $R^{313}$ groups on the same atom adjacent to the $X^3$, $X^4$, $X^5$, $X^6$ and/or N—$R^{31}$, and/or adjacent to the $X^8$, may form a ring, preferably a substituted or unsubstituted $C_3$-$C_6$ saturated carbocyclic ring together with the atom to which they are attached (such as a substituted or unsubstituted cyclopropyl ring or a substituted or unsubstituted cyclobutyl ring).

In some cases an R group in the ring system may form a ring with another R group on an adjacent and/or proximal atom, although in most embodiments this is not preferred. Thus, in some embodiments the following substituents may together form a ring: $R^1$ and $R^2$, $R^2$ and $R^3$, $R^3$ and $R^4$, $R^4$ and $R^5$, $R^5$ and $R^6$, $R^6$ and $R^7$. In the context of the present invention, an adjacent and/or proximal atom may mean another atom directly bonded to an atom (adjacent), or may be two atoms with only a single atom in between (proximal), or may mean two atoms close enough sterically to be capable of forming a ring (proximal). Preferably R groups attached to the same atom do not together form a ring, although this is not excluded. In some cases, any R group or L in the Y group may form a ring with any other group on a proximal atom, although this is not typical; the other group may be a group either in the ring system or in the Y group. Thus, in certain embodiments the following substituents may each together form a ring: $R^{31}$ and $R^{32}$, L and $R^{31}$ and/or L and $R^{32}$, $R^{31}$ with $R^{313}$, $R^{32}$ with $R^{313}$, and $R^{313}$ with another $R^{313}$. In addition, $R^1$ and L, $R^1$ and $R^{31}$, $R^1$ and $R^{32}$, $R^2$ and L, $R^2$ and $R^{31}$, $R^2$ and $R^{32}$, $R^3$ and L, $R^3$ and $R^{31}$, $R^3$ and $R^{32}$, $R^4$ and L, $R^4$ and $R^{31}$, $R^4$ and $R^{32}$, $R^5$ and L, $R^5$ and $R^{31}$, $R^5$ and $R^{32}$, $R^6$ and L, $R^6$ and $R^{31}$, $R^6$ and $R^{32}$, $R^7$ and L, $R^7$ and $R^{31}$, $R^7$ and $R^{32}$.

In the context of the present invention, a compound is considered to be a TDO inhibitor if its presence is capable of preventing, reducing or slowing the conversion of tryptophan into N-formylkynurenine by TDO as compared to the same conversion in its absence. Similarly, in the context of the present invention, a compound is considered to be an IDO inhibitor if its presence is capable of preventing, reducing or slowing the conversion of tryptophan into N-formylkynurenine by IDO as compared to the same conversion in its absence. The compounds of the invention may be selective TDO inhibitors, or selective IDO inhibitors, or may be inhibitors of both IDO and TDO.

In typical embodiments, the invention provides a compound as defined above comprising one or other of the following formulae:

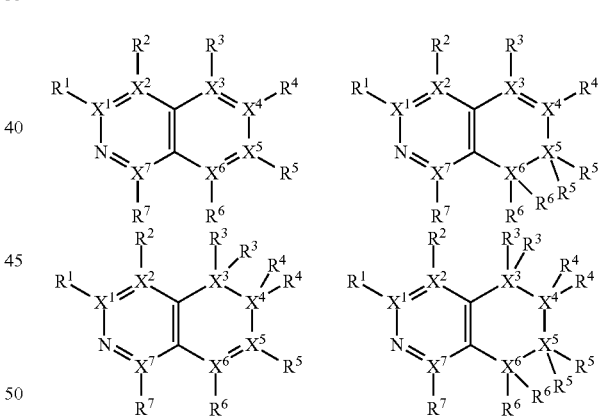

where each of the variables R and X has the same meaning as above and below herein. Thus, in typical embodiments the compound takes the form of a substituted fused heterocyclic compound wherein the ring system comprises an aromatic 6-membered heterocyclic ring fused to an aromatic, unsaturated, or saturated, carbocyclic or heterocyclic 6-membered ring.

In all of the embodiments of this invention (both above and below herein), the Y group is not especially limited, provided that it does not prevent the TDO or IDO inhibitory function from occurring. In certain typical embodiments, both above and in the following, the Y group comprises an aminocarbonyl group, a carbonylamino group, an aminosulphonyl group, a sulphonylamino group, a piperidinyl group and/or a piperazinyl group.

In all of the embodiments of this invention (both above and below herein), unless otherwise specified, a substituent (such as any R group, X group, or any other substituent) is not especially limited, provided that it does not prevent the TDO or IDO inhibitory function from occurring. In all of the embodiments mentioned in connection with this invention, both above and in the following, unless otherwise specified, the substituents are selected from H and an organic group. Thus, both above and in the following, the terms 'substituent' and 'organic group' are not especially limited and may be any functional group or any atom, especially any functional group or atom common in organic chemistry. Thus, 'substituent' and 'organic group' may have any of the following meanings.

The substituent or organic group may comprise any organic group and/or one or more atoms from any of groups IIIA, IVA, VA, VIA or VIIA of the Periodic Table, such as a B, Si, N, P, O, or S atom (e.g. OH, OR, $NH_2$, NHR, $NR_2$, SH, SR, $SO_2R$, $SO_3H$, $PO_4H_2$) or a halogen atom (e.g. F, Cl, Br or I) where R is a substituted or unsubstituted linear or branched lower hydrocarbon (1-6 C atoms) or a substituted or unsubstituted linear or branched higher hydrocarbon (7 C atoms or more, e.g. 7-40 C atoms).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups.

When the hydrocarbon comprises a cyclic group it may comprise an aromatic ring, a non-aromatic ring, an aliphatic ring, a heterocyclic group, and/or fused ring derivatives of these groups. The ring may be fully saturated, partially saturated, or fully unsaturated. The cyclic group may thus comprise a benzene, naphthalene, anthracene, phenanthrene, phenalene, biphenylene, pentalene, indene, as-indacene, s-indacene, acenaphthylene, fluorene, fluoranthene, acephenanthrylene, azulene, heptalene, pyrrole, pyrazole, imidazole, 1,2,3-triazole, 1,2,4-triazole, tetrazole, pyrrolidine, furan, tetrahydrofuran, 2-aza-tetrahydrofuran, 3-aza-tetrahydrofiiran, oxazole, isoxazole, furazan, 1,2,4-oxadiazol, 1,3,4-oxadiazole, thiophene, isothiazole, thiazole, thiolane, pyridine, pyridazine, pyrimidine, pyrazine, piperidine, 2-azapiperidine, 3-azapiperidine, piperazine, pyran, tetrahydropyran, 2-azapyran, 3-azapyran, 4-azapyran, 2-aza-tetrahydropyran, 3-aza-tetrahydropyran, morpholine, thiopyran, 2-azathiopyran, 3-azathiopyran, 4-azathiopyran, thiane, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene, as well as regioisomers of the above groups. These groups may generally be attached at any point in the group, and also may be attached at a hetero-atom or at a carbon atom. In some instances particular attachment points are preferred, such as at 1-yl, 2-yl and the like, and these are specified explicitly where appropriate. All tautomeric ring forms are included in these definitions. For example pyrrole is intended to include 1H-pyrrole, 2H-pyrrole and 3H-pyrrole.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The lower hydrocarbon group may be a methyl, ethyl, propyl, butyl, pentyl or hexyl group or regioisomers of these, such as isopropyl, isobutyl, tert-butyl, etc. The number of atoms in the ring of the cyclic group is not especially limited, but preferably the ring of the cyclic group comprises from 3-10 atoms, such as 3, 4, 5, 6, 7, 8, 9 or 10 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, sulphonyl groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

The invention will now be explained in more detail, by way of example only, with reference to the following Figures.

FIG. 1 shows a schematic diagram of tryptophan catabolism along the KP (from "The Kynurenine Pathway in Brain Tumour Pathogenesis", Adam et al., 2012, Cancer Res 72:5649-57).

Figure 2:
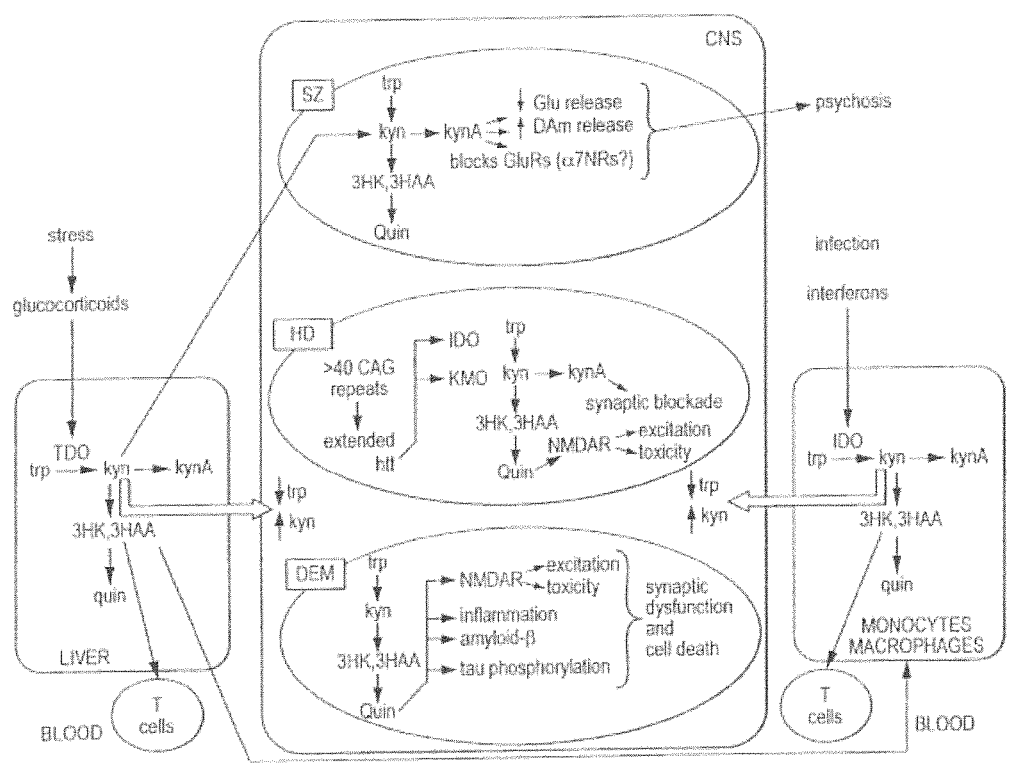

FIG. 2 shows a schematic summary of the involvement of kynurenine in CNS disorders (from "The kynurenine pathway as a therapeutic target in cognitive and neurodegenerative disorders", Stone and Darlington. Br. J. Pharmacol. 2013 169(6):1211-27.

The invention will now be described in more detail. Firstly a number of typical general structures of the compounds of the invention will be described.

As has been described, the invention relates to a compound for use in medicine for inhibiting tryptophan-2,3-dioxygenase (TDO) and/or indoleamine-2,3-dioxygenase (IDO), which compound comprises the following formula:

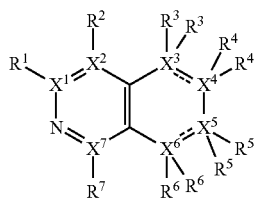

wherein $X^1$, $X^2$, and $X^7$, may be the same or different and each is independently selected from C and N; $X^3$, $X^4$, $X^5$, and $X^6$ may be the same or different and each is independently selected from C, N, O and S wherein when $X^3$ is N it has a double bond and wherein when $X^6$ is N it has a double bond; the dotted line is a bond which may be present or absent; $R^1$, $R^2$, $R^3$, $R^4$, $R^5$, $R^6$, and $R^7$ may be present or absent and may be the same or different and each is independently selected from H and a substituted or unsubstituted organic group, provided that at least one of $R^2$, $R^3$, $R^4$ and $R^6$ comprises a group Y; and provided that the number of $R^1$, $R^2$, $R^3$, $R^4$, $R^5$, $R^6$, and $R^7$ groups present is such that the respective valencies of $X^1$, $X^2$, $X^3$, $X^4$, $X^5$, $X^6$, and $X^7$ are maintained; and wherein Y is a group having a formula selected from the following:

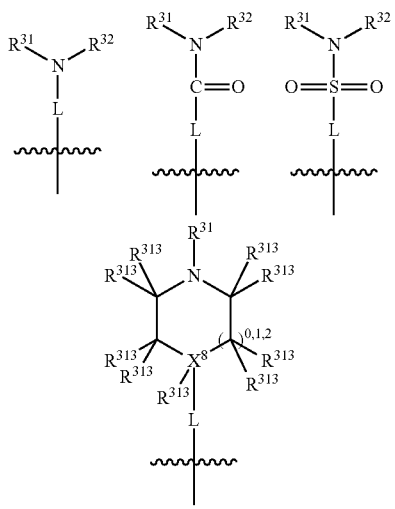

wherein L may be present or absent, and may be a substituted or unsubstituted organic linking group, and $R^{31}$ and $R^{32}$ may be the same or different and are selected from H and a substituted or unsubstituted organic group, $X^8$ is selected from C and N, and each $R^{313}$ may be the same or different and is selected from H and a substituted or unsubstituted organic group.

The fused bicyclic ring system is preferably aromatic. All tautomeric forms of the ring system (including the tautomeric form of each of the two 6-membered rings) are included. Alternatively, the right hand ring may be non-aromatic if it is unsaturated. In this latter case one or both of the bonds represented by the dotted lines are absent.

The group L is a linking group and is not especially limited provided that it does not impair the IDO or TDO inhibitory activity of the compounds. It may be present or absent. When absent, the N group (or CO, or $SO_2$, or $X^8$) of group Y is directly attached to the ring system. When present, L may be divalent, such that it may simply link the N atom of group Y to the ring system. Alternatively L may be trivalent if in addition it forms a ring with $R^{31}$ or $R^{32}$, and further alternatively L may be quadravalent if it forms a ring with both $R^{31}$ and $R^{32}$.

In typical embodiments, $X^3$, $X^4$, $X^5$ and $X^6$ are all C atoms. In other typical embodiments, one of $X^3$, $X^4$, $X^5$ and $X^6$ is N.

In typical embodiments both above and below herein, $X^3$ and/or $X^6$ is a C atom.

In typical embodiments, $X^1$, $X^2$, and $X^7$ are all C atoms. In other typical embodiments, one of $X^1$, $X^2$, and $X^7$ is N.

In typical embodiments both above and below herein, $X^7$ is a C atom. In other typical embodiments $X^7$ is an N atom.

In typical embodiments both above and below herein, Y comprises an aminocarbonyl group, a carbonylamino group, an aminosulphonyl group, a sulphonylamino group, a piperidinyl group and/or a piperazinyl group.

In typical embodiments both above and below herein, L is absent. In alternative typical embodiments L may comprise a substituted or unsubstituted $C_1$-$C_6$ alkylene group (such as —$CH_2$—, —$CH_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$—).

Thus, in view of the typical compounds already described, in more typical embodiments the compound used in the invention may comprise one of the following formulae:

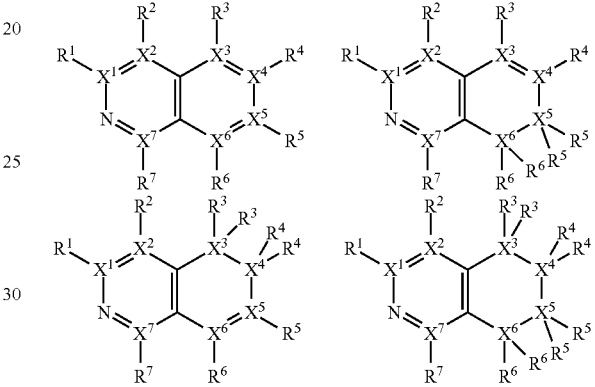

wherein, in each case, the substituents R and X are as defined in any of the above and below embodiments described herein.

Furthermore, in view of the typical compounds already described, in more typical embodiments the compound used in the invention may comprise one of the following formulae:

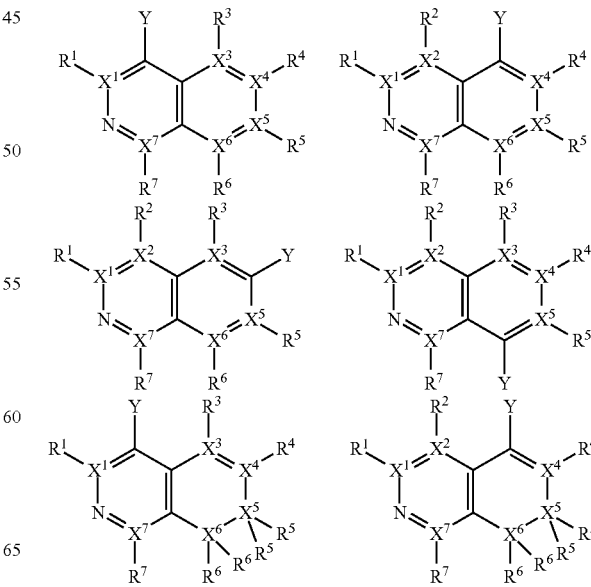

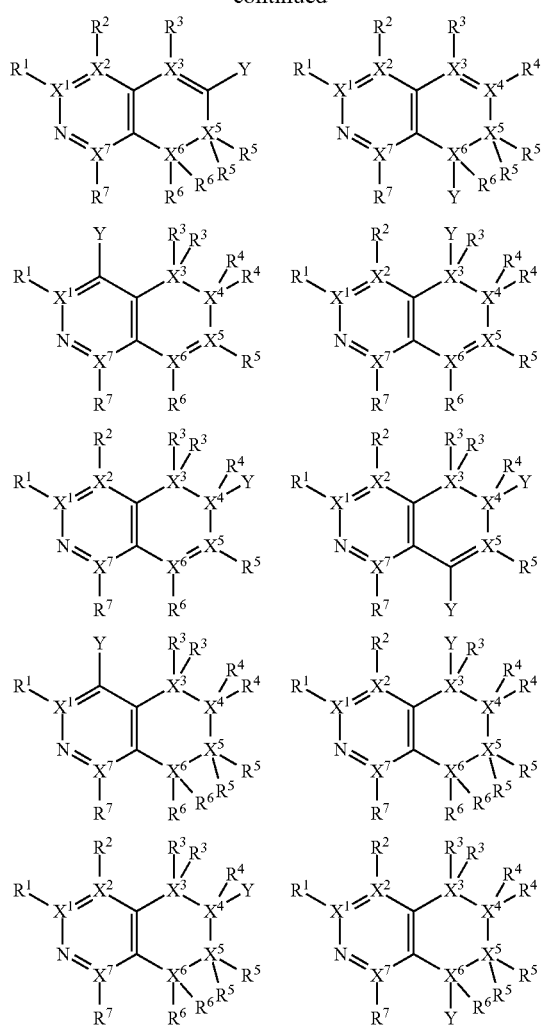

wherein, in each case, the substituents Y and R are as defined in any of the above or below embodiments described herein.

Furthermore, in view of the typical compounds already described, in more typical embodiments the compound used in the invention may comprise one of the following formulae:

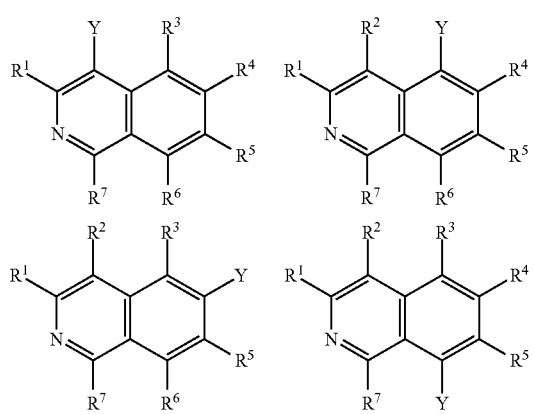

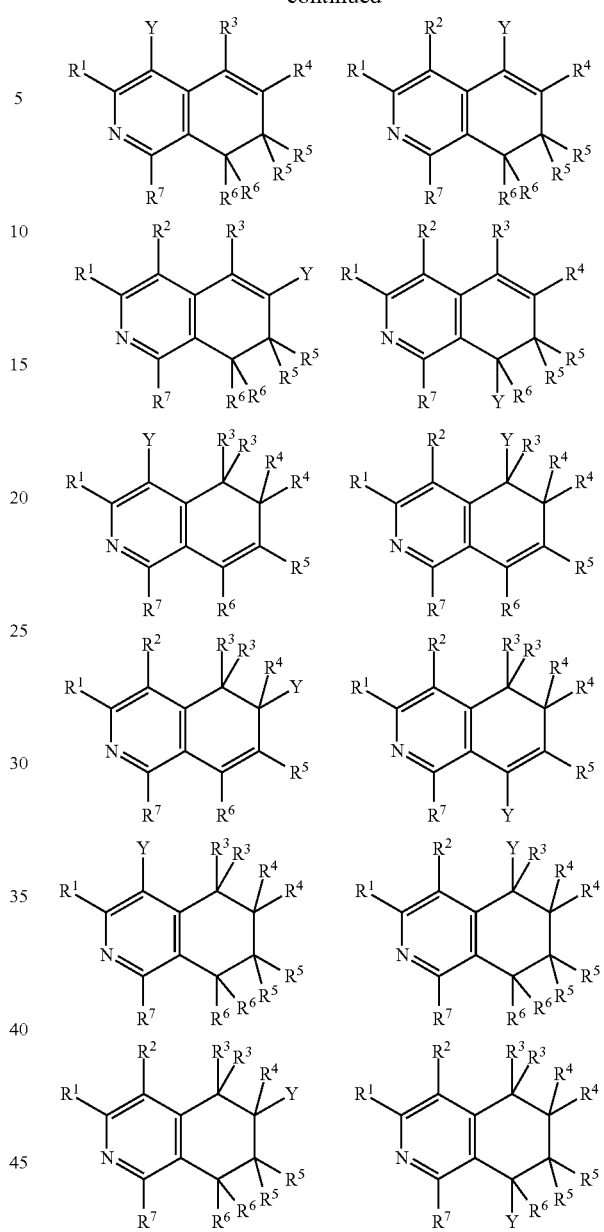

wherein, in each case, the substituents Y and R are as defined in any of the above or below embodiments described herein.

Furthermore, in view of the typical compounds already described, in more typical embodiments the compound used in the invention may comprise one of the following formulae:

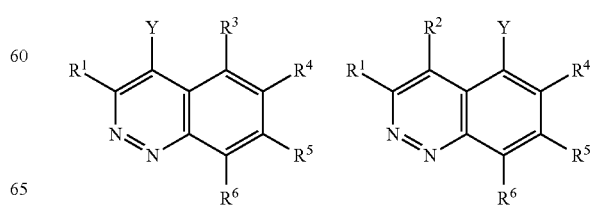

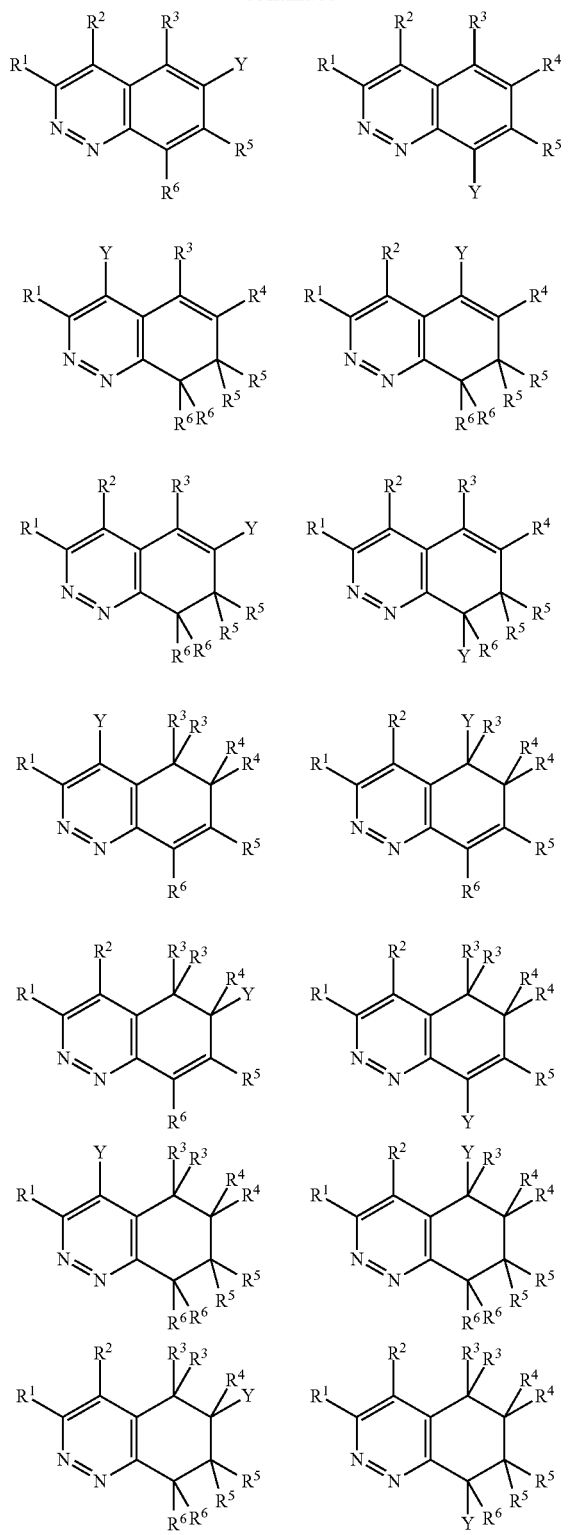
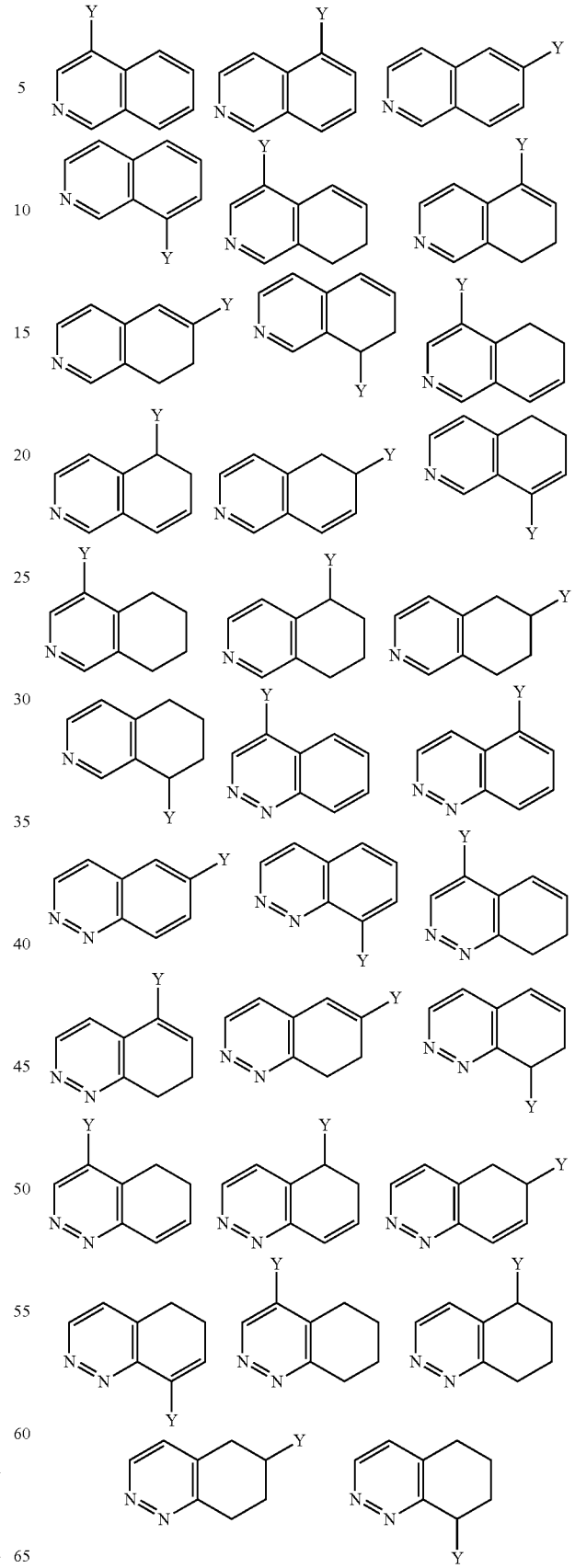
wherein, in each case, the substituents Y and R are as defined in any of the above or below embodiments described herein.
Furthermore, in view of the typical compounds already described, in more typical embodiments the compound used in the invention may comprise one of the following formulae:

wherein, in each case, the substituent Y is as defined in any of the above or below embodiments described herein.

In the compounds of the formula:

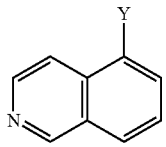

typically Y may be any of the Y groups described herein, but is preferably not a group of the following formula:

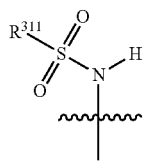

wherein $R^{311}$ comprises a phenyl group which itself has a substituent comprising a substituted or unsubstituted 2-oxo-dihydroquinoline group.

The Y, R and X groups in all of the compounds and structures both above and below herein will now be described in more detail.

As has been mentioned, the number of R substituents on an X or a ring atom will depend on its valency. Thus, it will be apparent in all of the embodiments of the invention, both above and below, that an X will have no substituents if it is O or S, no substituents or 1 substituent if it is N and 1 substituent or 2 substituents if it is C. The substituents are selected from H and an organic group as defined herein.

As has been mentioned, in all of the embodiments of this invention (both above and below herein), the substituent is not especially limited, provided that it does not prevent the TDO or IDO inhibitory function from occurring. However, in typical embodiments, the substituents may be selected independently as follows:

$R^1$, $R^2$, $R^3$, $R^4$, $R^5$, $R^6$, $R^7$, and $R^{313}$ are typically each independently selected from H and a group selected from the following groups:

a halogen (such as —F, —Cl, —Br and —I);

a nitrile group;

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);

a substituted or unsubstituted linear or branched $C_1$-$C_6$ halogenated alkyl group (such as —$CH_2$F, —$CH_2$Cl, —$CH_2$Br, —$CH_2$I, —$CF_3$, —$CCl_3$—$CBr_3$, —$CI_3$, —$CH_2CF_3$, —$CH_2CCl_3$, —$CH_2CBr_3$, and —$CH_2CI_3$);

an —$NH_2$ or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)$F_2$-Ph, —NH-2,(3,4,5 or 6)$Cl_2$-Ph, —NH-2,(3,4,5 or 6)$Br_2$-Ph, —NH-2,(3,4,5 or 6)$I_2$-Ph, —NH-2,(3,4,5 or 6)$Me_2$-Ph, —NH-2,(3,4,5 or 6)$Et_2$-Ph, —NH-2,(3,4,5, or 6)$Pr_2$-Ph, —NH-2,(3,4,5 or 6)$Bu_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH group, or a substituted or unsubstituted linear or branched $C_1$-$C_6$ alcohol group (such as —$CH_2$OH, —$CH_2CH_2$OH, —$CH_2CH_2CH_2$OH, —$CH_2CH_2CH_2CH_2$OH, —$CH_2CH_2CH_2CH_2CH_2$OH, and —$CH_2CH_2CH_2CH_2CH_2CH_2$OH);

a substituted or unsubstituted linear or branched $C_1$-$C_6$ carboxylic acid group (such as —COOH, —$CH_2$COOH, —$CH_2CH_2$COOH, —$CH_2CH_2CH_2$COOH, —$CH_2CH_2CH_2CH_2$COOH, and —$CH_2CH_2CH_2CH_2CH_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)$CH_2$Ph, —(CO)$CH_2$OH, —(CO)$CH_2OCH_3$, —(CO)$CH_2NH_2$, —(CO)$CH_2$NHMe, —(CO)$CH_2NMe_2$, —(CO)-cyclopropyl, —(CO)-1,3-epoxypropan-2-yl; —(CO)$NH_2$, —(CO)NHMe, —(CO)$NMe_2$, —(CO)NHEt, —(CO)$NEt_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2NH_2$, —(CO)NHCH$_2$CH$_2$NHMe, and —(CO)NHCH$_2$CH$_2NMe_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2$COOMe, —$CH_2CH_2$COOMe, —$CH_2CH_2CH_2$COOMe, and —$CH_2CH_2CH_2CH_2$COOMe);

a substituted or unsubstituted linear or branched $C_1$-$C_6$ amide group (such as —CO—$NH_2$, —CO—NMeH, —CO—$NMe_2$, —CO—NEtH, —CO—NEtMe, —CO—$NEt_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$— cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe;

an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a substituted or unsubstituted saturated or unsaturated heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrimidin-6-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl); and where there are two $R^{313}$ groups attached to the same atom, they may together form a group which is double bonded to that atom, (such as a carbonyl group (=O) or an alkene group (=C(R')$_2$) wherein each R' group is the same or different and is H or an organic group, preferably H or a straight or branched $C_1$-$C_6$ alkyl group), or the two $R^{313}$ groups on the same atom may form a ring, preferably a substituted or unsubstituted $C_3$-$C_6$ saturated carbocyclic ring together with the atom to which they are attached (such as a substituted or unsubstituted cyclopropyl ring or a substituted or unsubstituted cyclobutyl ring), this being more preferable when the two $R^{313}$ groups are on an atom adjacent to the N—$R^{31}$, and/or adjacent to the $X^8$.

More typically, where present, $R^1$ and $R^7$ are independently selected from H, a substituted or unsubstituted $C_1$-$C_6$ alkyl group, an —NH$_2$ group and a substituted or unsubstituted $C_1$-$C_6$ amino group, and a substituted or unsubstituted $C_1$-$C_6$ alkoxy group. More typically, where present $R^2$, $R^3$, $R^4$, and $R^6$ are independently selected from H, a halogen (such as —F, —Cl and —Br) a substituted or unsubstituted $C_1$-$C_6$ alkyl group, an —NH$_2$ group and a substituted or unsubstituted $C_1$-$C_6$ amino group, a substituted or unsubstituted $C_1$-$C_6$ alkoxy group, a nitrile group, and a substituted or unsubstituted phenyl group. More typically, where present, $R^5$ is selected from H, a halogen (such as —F, —Cl and —Br) a substituted or unsubstituted $C_1$-$C_6$ alkyl group, an group and a substituted or unsubstituted $C_1$-$C_6$ amino group, a substituted or unsubstituted $C_1$-$C_6$ alkoxy group, a nitrile group, a substituted or unsubstituted aromatic or aliphatic cyclic group (such as a carbocyclic group or a heterocyclic group, such as a substituted or unsubstituted phenyl group). More typically each $R^{313}$ is selected from H, a halogen (such as —F and —Cl) a substituted or unsubstituted $C_1$-$C_6$ alkyl group, an —NH, group and a substituted or unsubstituted $C_1$-$C_6$ amino group, a substituted or unsubstituted $C_1$-$C_6$ alkoxy group, a nitrile group, a substituted or unsubstituted aromatic or aliphatic cyclic group (such as a carbocyclic group or a heterocyclic group, such as a substituted or unsubstituted phenyl group). Most typically each $R^{313}$ is selected from H and a substituted or unsubstituted $C_1$-$C_6$ alkyl group. In certain embodiments, where present all of $R^1$, $R^2$, $R^3$, $R^4$, $R^5$, $R^6$, $R^7$ and $R^{313}$ are H, or one of $R^1$, $R^2$, $R^3$, $R^4$, $R^5$, $R^6$, and $R^7$ is not H and all of $R^{313}$ are H.

As has been mentioned at least one of $R^2$, $R^3$, $R^4$ and $R^6$ comprises a group Y having the following formula:

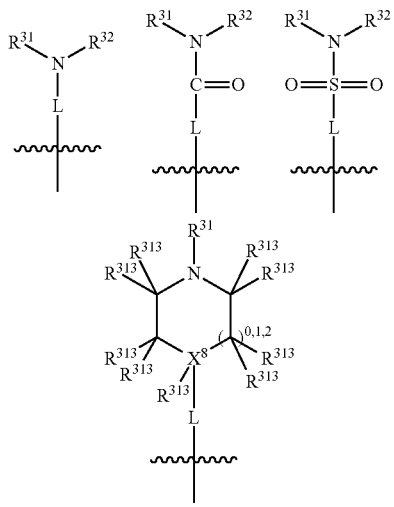

wherein L may be present or absent, and may be any substituted or unsubstituted organic linking group; $R^{31}$ and $R^{32}$ may be the same or different and are selected from H and a substituted or unsubstituted organic group; $X^8$ is selected from C and N; and each $R^{313}$ may be the same or different and is selected from H and a substituted or unsubstituted organic group. In the present context, any group may be a linking group provided that it is capable of joining the ring system to the rest of the Y group. Typically the linking group is divalent, but may be trivalent or tetravalent in some embodiments. In some typical embodiments, $R^{32}$ is H:

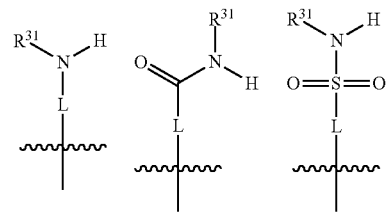

or $R^{31}$ is H:

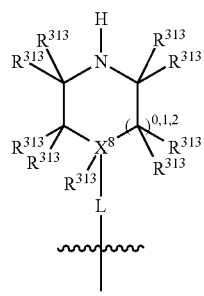

As has been mentioned, in typical embodiments, the group L may be present or absent. When present L is a linker group attaching Y to the ring system. L is not especially limited, provided that the function of the molecule is not impaired. Accordingly, any known linking groups in organic chemistry may be employed. Typically L is a divalent group, suitable for linking the ring system to the group Y. In such embodiments L may, for example, comprise a substituted or unsubstituted $C_1$-$C_6$ alkylene group (such as —$CH_2$—, —$CH_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$—).

The group Y typically comprises an aminocarbonyl group, a carbonylamino group, an aminosulphonyl group, a sulphonylamino group, a piperidinyl group and/or a piperazinyl group. Typically the N atom in the above formula for Y forms the amino part of these groups, although it is not excluded that the N atom is not the amino part of these groups.

In some typical such embodiments L is absent, and Y may be selected from the following groups:

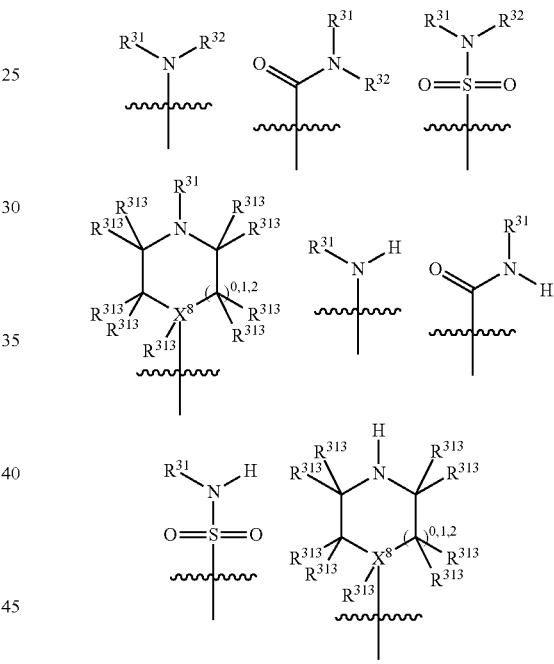

Alternatively, an aminocarbonyl group or an aminosulphonyl group may be present when $R^{31}$ (or $R^{32}$) comprises a carbonyl group or a sulphonyl group. In such cases, typically the carbonyl group or the sulphonyl group is attached to the N atom of Y. For example, in certain embodiments, $R^{31}$ (or $R^{32}$) may comprise one of the following groups:

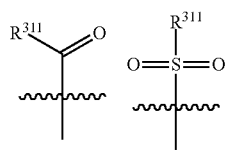

wherein $R^{311}$ is selected from H and a substituted or unsubstituted organic group. In such cases, the Y group is typically selected from the following:

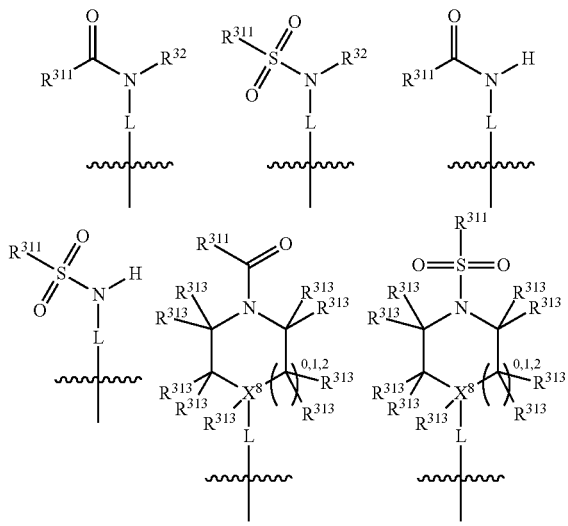

where L is present and L, $R^{32}$, $R^{311}$ and $R^{313}$ have the same meaning as anywhere above or below herein. In typical embodiments, $R^{311}$ is selected from the following:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —CH₂Ph, —CH₂(2,3 or 4)F-Ph, —CH₂(2,3 or 4)Cl-Ph, —CH₂(2,3 or 4)Br-Ph, —CH₂(2,3 or 4)I-Ph, —CH₂CH₂Ph, —CH₂CH₂CH₂Ph, —CH₂CH₂CH₂CH₂Ph, —CH₂CH₂CH₂CH₂CH₂Ph, and —CH₂CH₂CH₂CH₂CH₂CH₂Ph);

a substituted or unsubstituted linear or branched $C_1$-$C_6$ halogenated alkyl group (such as —CH₂F, —CF₃, —CH₂CF₃);

an —NH₂ or a substituted or unsubstituted linear or branched primary secondary or tertiary $C_1$-$C_6$ amine group (such as —NMeH, —NMe₂, —NEtH, —NEtMe, —NEt₂, —NPrH, —NPrMe, —NPrEt, —NPr₂, —NBuH, —NBuMe, —NBuEt, —CH₂—NH₂, —CH₂—NMeH, —CH₂—NMe₂, —CH₂—NEtH, —CH₂—NEtMe, —CH₂—NEt₂, —CH₂—NPrH, —CH₂—NPrMe, and —CH₂—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F₂-Ph, —NH-2,(3,4,5 or 6)Cl₂-Ph, —NH-2,(3,4,5 or 6)Br₂-Ph, —NH-2,(3,4,5 or 6)I₂-Ph, —NH-2,(3,4,5 or 6)Me₂-Ph, —NH-2,(3,4,5 or 6)Et₂-Ph, —NH-2,(3,4,5, or 6)Pr₂-Ph, —NH-2,(3,4,5 or 6)Bu₂-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted linear or branched $C_1$-$C_6$ alcohol group (such as —CH₂OH, —CH₂CH₂OH, —CH₂CH₂CH₂OH, —CH₂CH₂CH₂CH₂OH, —CH₂CH₂CH₂CH₂CH₂OH, and —CH₂CH₂CH₂CH₂CH₂CH₂OH);

a substituted or unsubstituted linear or branched $C_1$-$C_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;

a substituted or unsubstituted linear or branched C alkoxy or aryloxy group (such as —OMe, —OEt, —OPr, —O-i-Pr, —O-n-Bu, —O-i-Bu, —O-t-Bu, —O-pentyl, —O-hexyl, —OCH₂F, —OCHF₂, —OCF₃, —O-Ph, —O—CH₂-Ph, —O—CH₂-(2,3 or 4)-F-Ph, —O—CH₂-(2,3 or 4)-Cl-Ph, —CH₂OMe, —CH₂OEt, —CH₂OPr, —CH₂OBu, —CH₂CH₂OMe, —CH₂CH₂CH₂OMe, —CH₂CH₂CH₂CH₂OMe, and —CH₂CH₂CH₂CH₂CH₂OMe);

a substituted or unsubstituted linear or branched aminoalkoxy group (such as —OCH₂CH₂NH₂, —OCH₂CH₂NHMe, —OCH₂CH₂NMe₂, —OCH₂CH₂NHEt, and —OCH₂CH₂NEt₂;

a substituted or unsubstituted aminosulphonyl group (such as —NHSO₂Me, —NHSO₂Et, —NHSO₂Pr, —NHSO₂iPr, —NHSO₂Ph, —NHSO₂-(2,3 or 4)-F-Ph, —NHSO₂-cyclopropyl, —NHSO₂CH₂CH₂OCH₃);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F₂-Ph-, 2,(3,4,5 or 6)-Cl₂-Ph-, 2,(3,4,5 or 6)-Br₂-Ph-, 2,(3,4,5 or 6)-I₂-Ph-, 2,(3,4,5 or 6)-Me₂-Ph-, 2,(3,4,5 or 6)-Et₂-Ph-, 2,(3,4,5 or 6)-Pr₂-Ph-, 2,(3,4,5 or 6)-Bu₂-Ph-, 2,(3,4,5 or 6)-(CN)₂-Ph-, 2,(3,4,5 or 6)-(NO₂)₂-Ph-, 2,(3,4,5 or 6)-(NH₂)₂-Ph-, 2,(3,4,5 or 6)-(MeO)₂-Ph-, 2,(3,4,5 or 6)-(CF₃)₂-Ph-, 3,(4 or 5)-F₂-Ph-, 3,(4 or 5)-Cl₂-Ph-, 3,(4 or 5)-Br₂-Ph-, 3,(4 or 5)-h-Ph-, 3,(4 or 5)-Me₂-Ph-, 3,(4 or 5)-Et₂-Ph-, 3,(4 or 5)-Pr₂-Ph-, 3,(4 or 5)-Bu₂-Ph-, 3,(4 or 5)-(CN)₂-Ph-, 3,(4 or 5)-(NO₂)₂-Ph-, 3,(4 or 5)-(NH₂)₂-Ph-, 3,(4 or 5)-(MeO)₂-Ph-, 3,(4 or 5)-(CF₃)₂-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO₂)-Ph-, 3-(NO₂)-Ph-, 4-(NO₂)-Ph-, 2-(NH₂)-Ph-, 3-(NH₂)-Ph-, 4-(NH₂)-Ph-, 2-MeO-Ph-, 3-MeO-Ph-, 4-MeO-Ph-, 2-(NH₂—CO)-Ph-, 3-(NH₂—CO)-Ph-, 4-(NH₂—CO)-Ph-, 2-CF₃-Ph-, 3-CF₃-Ph-, 4-CF₃-Ph-, 2-CF₃O-Ph-, 3-CF₃O-Ph-, and 4-CF₃O-Ph-);

a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).

In more preferred embodiments, $R^{311}$ is selected from the following:
  a substituted or unsubstituted linear or branched $C_1$-$C_6$ alkyl group (such as Me, Et, Pr, i-Pr, n-Bu, i-Bu, t-Bu, pentyl and hexyl);
  a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
  a substituted or unsubstituted cyclic $C_3$-$C_8$ alkyl group (such as cyclopropyl, cyclobutyl, cyclopentyl, cyclohexyl, cycloheptyl and cyclooctyl);
  a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);
  a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).

In these cases, typically L does not comprise a carbonyl or a sulphonyl, although this is not excluded.

In typical embodiments, the linker L is absent. In such cases, Y may be selected from any of the following:

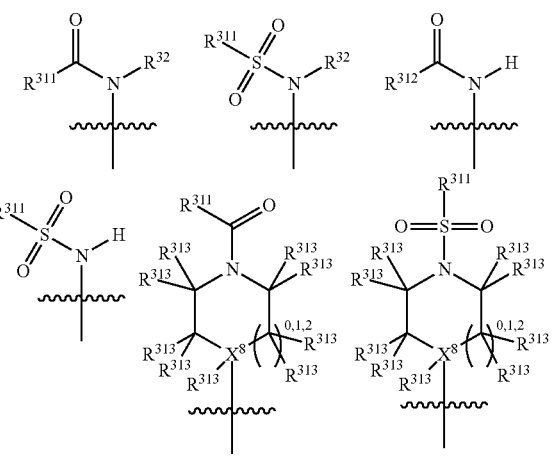

wherein $R^{32}$ is selected from a substituted or unsubstituted organic group (in these cases $R^{32}$ is not H) and $R^{311}$ and $R^{313}$ are as defined anywhere herein.

In the present context $R^{312}$ is selected from the following:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched $C_1$-$C_6$ halogenated alkyl group (such as —CH$_2$F, —CF$_3$, —CH$_2$CF$_3$);

an —NH$_2$ or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted linear or branched $C_1$-$C_6$ alcohol group (such as —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched $C_1$-$C_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted 6 membered carbocyclic or heterocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph-, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-, pyridin-2-yl, pyridine-3-yl, pyridin-4-yl, pyrimidin-2-yl, pyrimidin-5-yl, pyrimidin-4-yl, pyridazin-3-yl, pyridazine-4-yl); and a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

In more typical embodiments $R^{312}$ is selected from:

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted 6 membered carbocyclic or heterocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph-, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-b-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-, pyridin-2-yl, pyridine-3-yl, pyridin-4-yl, pyrimidin-2-yl, pyrimidin-5-yl, pyrimidin-4-yl, pyridazin-3-yl, pyridazine-4-yl); and a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

In other typical embodiments, the piperidine and piperazine substituents that comprise Y may be selected from any of the following:

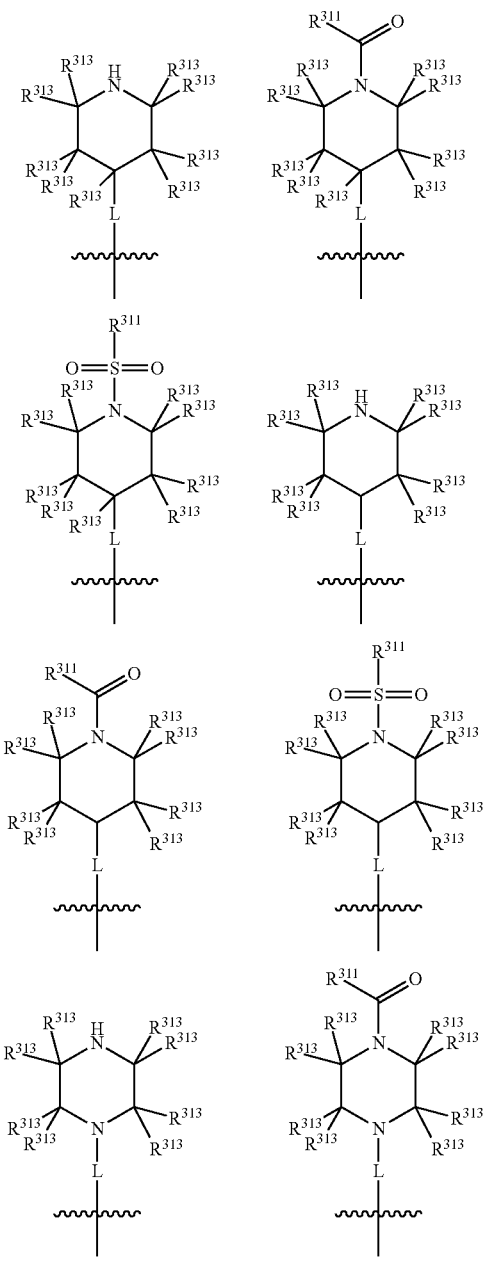

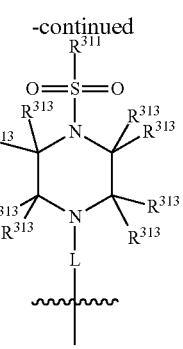

wherein in each case L may be present or absent.

As has been mentioned, in some cases L may form a ring with R$^{31}$ or R$^{32}$, and/or R$^{31}$ and R$^{32}$ may form a ring with each other. In some such embodiments, the Y group may be selected from the following structures:

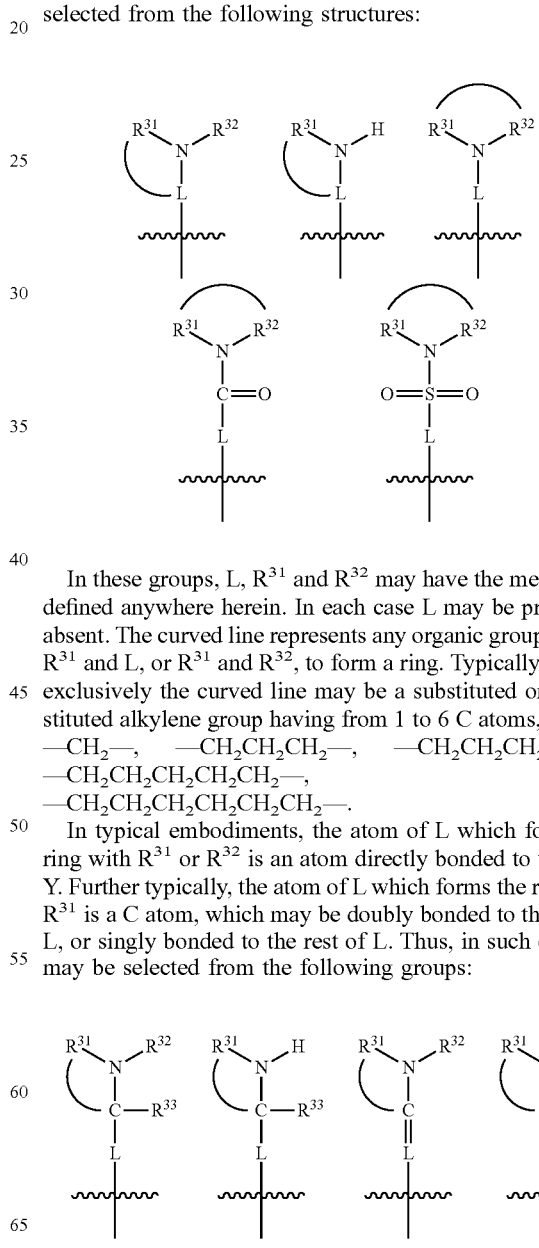

In these groups, L, R$^{31}$ and R$^{32}$ may have the meaning as defined anywhere herein. In each case L may be present or absent. The curved line represents any organic group joining R$^{31}$ and L, or R$^{31}$ and R$^{32}$, to form a ring. Typically, but not exclusively the curved line may be a substituted or unsubstituted alkylene group having from 1 to 6 C atoms, such as —CH$_2$—, —CH$_2$CH$_2$CH$_2$—, —CH$_2$CH$_2$CH$_2$CH$_2$—, —CH$_2$CH$_2$CH$_2$CH$_2$CH$_2$—, and —CH$_2$CH$_2$CH$_2$CH$_2$CH$_2$CH$_2$—.

In typical embodiments, the atom of L which forms the ring with R$^{31}$ or R$^{32}$ is an atom directly bonded to the N of Y. Further typically, the atom of L which forms the ring with R$^{31}$ is a C atom, which may be doubly bonded to the rest of L, or singly bonded to the rest of L. Thus, in such cases, Y may be selected from the following groups:

where $R^{33}$ may be selected from H and a substituted or unsubstituted organic group. In the case where L is double bonded at one end, such as to C in the above, then the valency of L is maintained. In such cases, L is trivalent rather than divalent, and may comprise a substituted or unsubstituted $C_1$-$C_6$ alkenyl group (such as =CH—, =CHCH$_2$—, =CHCH$_2$CH$_2$—, =CHCH$_2$CH$_2$CH$_2$—, =CHCH$_2$CH$_2$CH$_2$CH$_2$—, and =CHCH$_2$CH$_2$CH$_2$CH$_2$CH$_2$—).

In some cases, the rest of the linker, L, is absent (in these cases the linker comprises only the C atom which forms the ring with $R^{31}$, or comprises only —$CR^{33}$— when $R^{33}$ is present):

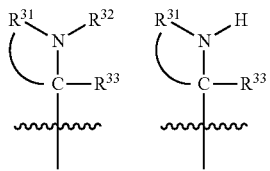

In typical embodiments of the invention, both above and below herein, $R^{31}$ and $R^{32}$ are each independently selected from H and the following groups:

- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CF$_3$, and —CH$_2$CF$_3$);
- a substituted or unsubstituted cyclic amine or amido group (such as pyrrolidin-2-yl, pyrrolidin-3-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_2$-$C_6$ alcohol group (such as —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, and —CH$_2$CH$_2$CH$_2$CH$_2$CH$_2$CH$_2$OH);
- a substituted or unsubstituted linear or branched C alkoxy or aryloxy group linked through —O via at least two further C atoms (such as —CH$_2$CH$_2$OPh, —CH$_2$CH$_2$OMe, —CH$_2$CH$_2$OEt, —CH$_2$CH$_2$OPr, —CH$_2$CH$_2$OBu, —CH$_2$CH$_2$CH$_2$OPh, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched $C_2$-$C_6$ carboxylic acid group (such as —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
- a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
- a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrrolidine-N-yl, —SO$_2$-morpholine-N-yl, —SO$_2$NHCH$_2$OMe, and —SO$_2$NHCH$_2$CH$_2$OMe;
- a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and
- a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).

Independently, in typical embodiments of the invention, $R^{33}$ is selected from H and the following groups:
- a substituted or unsubstituted linear or branched $C_1$-$C_6$ alkyl group (such as Me, Et, Pr, r, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CH$_2$Cl, —CH$_2$Br, —CH$_2$I, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$);
- an —NH$_2$ or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);
- a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph,
- a substituted or unsubstituted cyclic amine or amino group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_1$-$C_6$ alcohol group (such as —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, and —CH$_2$CH$_2$CH$_2$CH$_2$CH$_2$CH$_2$OH);
- a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
- a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
- a substituted or unsubstituted linear or branched $C_1$-$C_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;
- a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CF$_2$NHEt, and —OCH$_2$CH$_2$NEt$_2$;
- a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$— cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrrolidine-N-yl, —SO$_2$-morpholine-N-yl, —SO$_2$NHCH$_2$OMe, and —SO$_2$NHCH$_2$CH$_2$OMe;

a substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a substituted or unsubstituted saturated or unsaturated heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrimidin-6-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl).

In more typical embodiments, $R^{31}$ (and/or $R^{32}$) is selected from a carbocyclic or heterocyclic group, which may be saturated or unsaturated, or aromatic or aliphatic, such as a substituted or unsubstituted phenyl group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-b-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); or such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1 yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

Typically, when the Y group comprises one of the following groups:

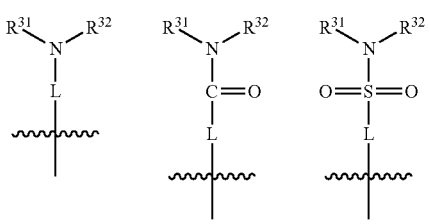

then $R^{31}$ (and/or $R^{32}$) is preferably selected from the following:

a substituted or unsubstituted linear or branched $C_1$-$C_6$ alkyl group (such as Me, Et, Pr, n-Bu, i-Bu, t-Bu, pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$P and —CH$_2$CH$_2$CH$_2$CH$_2$CH$_2$CH$_2$Ph);

a substituted or unsubstituted linear or branched C$_1$-C$_6$ halogenated alkyl group (such as —CH$_2$F, —CF$_3$, and —CH$_2$CF$_3$);

a substituted or unsubstituted cyclic amine or amido group (such as pyrrolidin-2-yl, pyrrolidin-3-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic C$_3$-C$_8$ alkyl group (such as cyclopropyl, cyclobutyl, cyclopentyl, cyclohexyl, cycloheptyl and cyclooctyl);

a substituted or unsubstituted linear or branched C$_2$-C$_6$ alcohol group (such as —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_7$ alkoxy or aryloxy group linked through —O via at least two further C atoms (such as —CH$_2$CH$_2$OPh, —CH$_2$CH$_2$OMe, —CH$_2$CH$_2$OEt, —CH$_2$CH$_2$OPr, —CH$_2$CH$_2$OBu, —CH$_2$CH$_2$CH$_2$OPh, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched C$_2$-C$_6$ carboxylic acid group (such as —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$— cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrrolidine-N-yl, —SO$_2$-morpholine-N-yl, —SO$_2$NHCH$_2$OMe, and —SO$_2$NHCH$_2$CH$_2$OMe;

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 34-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).

More preferably, when the Y group comprises one of the following groups:

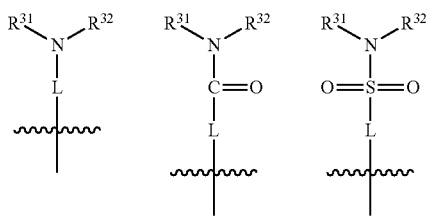

then R³¹ (and/or R³²) is preferably selected from a carbocyclic or heterocyclic group, which may be saturated or unsaturated, or aromatic or aliphatic, such as a substituted or unsubstituted phenyl group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F₂-Ph-, 2,(3,4,5 or 6)-Cl₂-Ph-, 2,(3,4,5 or 6)-Br₂-Ph-, 2,(3,4,5 or 6)-b-Ph-, 2,(3,4,5 or 6)-Me₂-Ph-, 2,(3,4,5 or 6)-Et₂-Ph-, 2,(3,4,5 or 6)-Pr₂-Ph-, 2,(3,4,5 or 6)-Bu₂-Ph-, 2,(3,4,5 or 6)-(CN)₂-Ph-, 2,(3,4,5 or 6)-(NO₂)₂-Ph-, 2,(3,4,5 or 6)-(NH₂)₂-Ph-, 2,(3,4,5 or 6)-(MeO)₂-Ph-, 2,(3,4,5 or 6)-(CF₃)₂-Ph-, 3,(4 or 5)-F₂-Ph-, 3,(4 or 5)-Cl₂-Ph-, 3,(4 or 5)-Br₂-Ph-, 3,(4 or 5)-I₂-Ph-, 3,(4 or 5)-Me₂-Ph-, 3,(4 or 5)-Et₂-Ph-, 3,(4 or 5)-Pr₂-Ph-, 3,(4 or 5)-Bu₂-Ph-, 3,(4 or 5)-(CN)₂-Ph-, 3,(4 or 5)-(NO₂)₂-Ph-, 3,(4 or 5)-(NH₂)₂-Ph-, 3,(4 or 5)-(MeO)₂-Ph-, 3,(4 or 5)-(CF₃)₂-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO₂)-Ph-, 3-(NO₂)-Ph-, 4-(NO₂)-Ph-, 2-(NH₂)-Ph-, 3-(NH₂)-Ph-, 4-(NH₂)-Ph-, 2-MeO-Ph-, 3-MeO-Ph-, 4-MeO-Ph-, 2-(NH₂—CO)-Ph-, 3-(NH₂—CO)-Ph-, 4-(NH₂—CO)-Ph-, 2-CF₃-Ph-, 3-CF₃-Ph-, 4-CF₃-Ph-, 2-CF₃O-Ph-, 3-CF₃O-Ph-, and 4-CF₃O-Ph-); or such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1 yl, tetrazole-2-yl, tetrazole-3-yl, tetrazole-4-yl, tetrazole-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl) or such as a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

Typically, when the Y group comprises the following group:

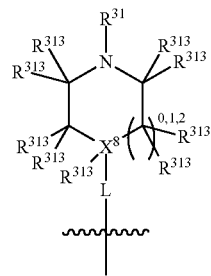

then R³¹ is typically a —COR³¹¹ group or an —SO₂R³¹¹ group:

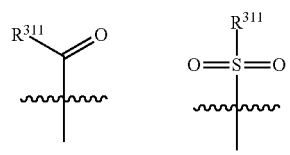

wherein R³¹¹ is selected from:
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH₂Ph, —CH₂(2,3 or 4)F-Ph, —CH₂(2,3 or 4)Cl-Ph, —CH₂(2,3 or 4)Br-Ph, —CH₂(2,3 or 4)I-Ph, —CH₂CH₂Ph, —CH₂CH₂CH₂Ph, —CH₂CH₂CH₂CH₂Ph, —CH₂CH₂CH₂CH₂CH₂Ph, and —CH₂CH₂CH₂CH₂CH₂CH₂Ph);
- a substituted or unsubstituted linear or branched $C_1$-$C_6$ halogenated alkyl group (such as —CH₂F, —CF₃, —CH₂CF₃);
- an —NH₂ or a substituted or unsubstituted linear or branched primary secondary or tertiary $C_1$-$C_6$ amine group (such as —NMeH, —NMe₂, —NEtH, —NEtMe, —NEt₂, —NPrH, —NPrMe, —NPrEt, —NPr₂, —NBuH, —NBuMe, —NBuEt, —CH₂—NH₂, —CH₂—NMeH, —CH₂—NMe₂, —CH₂—NEtH, —CH₂—NEtMe, —CH₂—NEt₂, —CH₂—NPrH, —CH₂—NPrMe, and CH₂—NPrEt);
- a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F₂-Ph, —NH-2,(3,4,5 or 6)Cl₂-Ph, —NH-2,(3,4,5 or 6)Br₂-Ph, —NH-2,(3,4,5 or 6)I₂-Ph, —NH-2,(3,4,5 or 6)Me₂-Ph, —NH-2,(3,4,5 or 6)Et₂-Ph, —NH-2,(3,4,5, or 6)Pr₂-Ph, —NH-2,(3,4,5 or 6)Bu₂-Ph,
- a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_1$-$C_6$ alcohol group (such as —CH₂OH, —CH₂CH₂OH, —CH₂CH₂CH₂OH, —CH₂CH₂CH₂CH₂OH, —CH₂CH₂CH₂CH₂CH₂OH, and —CH₂CH₂CH₂CH₂CH₂CH₂OH);
- a substituted or unsubstituted linear or branched $C_1$-$C_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;
- a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH₂F, —OCHF₂, —OCF₃, —O-Ph, —O—CH₂-Ph, —O—CH₂-(2,3 or 4)-F-Ph, —O—CH₂-(2,3 or 4)-Cl-Ph, —CH₂OMe, —CH₂OEt, —CH₂OPr, —CH₂OBu, —CH₂CH₂OMe, —CH₂CH₂CH₂OMe, —CH₂CH₂CH₂CH₂OMe, and —CH₂CH₂CH₂CH₂CH₂OMe);

a substituted or unsubstituted linear or branched aminoalkoxy group (such as —OCH₂CH₂NH₂, —OCH₂CH₂NHMe, —OCH₂CH₂NMe₂, —OCH₂CH₂NHEt, and —OCH₂CH₂NEt₂);

a substituted or unsubstituted aminosulphonyl group (such as —NHSO₂Me, —NHSO₂Et, —NHSO₂Pr, —NHSO₂iPr, —NHSO₂Ph, —NHSO₂-(2,3 or 4)-F-Ph, —NHSO₂-cyclopropyl, —NHSO₂CH₂CH₂OCH₃);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F₂-Ph-, 2,(3,4,5 or 6)-Cl₂-Ph-, 2,(3,4,5 or 6)-Br₂-Ph-, 2,(3,4,5 or 6)-I₂-Ph-, 2,(3,4,5 or 6)-Me₂-Ph-, 2,(3,4,5 or 6)-Et₂-Ph-, 2,(3,4,5 or 6)-Pr₂-Ph-, 2,(3,4,5 or 6)-Bu₂-Ph-, 2,(3,4,5 or 6)-(CN)₂-Ph-, 2,(3,4,5 or 6)-(NO₂)₂-Ph-, 2,(3,4,5 or 6)-(NH₂)₂-Ph-, 2,(3,4,5 or 6)-(MeO)₂-Ph-, 2,(3,4,5 or 6)-(CF₃)₂-Ph-, 3,(4 or 5)-F₂-Ph-, 3,(4 or 5)-Cl₂-Ph-, 3,(4 or 5)-Br₂-Ph-, 3,(4 or 5)-I₂-Ph-, 3,(4 or 5)-Me₂-Ph-, 3,(4 or 5)-Et₂-Ph-, 3,(4 or 5)-Pr₂-Ph-, 3,(4 or 5)-Bu₂-Ph-, 3,(4 or 5)-(CN)₂-Ph-, 3,(4 or 5)-(NO₂)₂-Ph-, 3,(4 or 5)-(NH₂)₂-Ph-, 3,(4 or 5)-(MeO)₂-Ph-, 3,(4 or 5)-(CF₃)₂-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO₂)-Ph-, 3-(NO₂)-Ph-, 4-(NO₂)-Ph-, 2-(NH₂)-Ph-, 3-(NH₂)-Ph-, 4-(NH₂)-Ph-, 2-MeO-Ph-, 3-MeO-Ph-, 4-MeO-Ph-, 2-(NH₂—CO)-Ph-, 3-(NH₂—CO)-Ph-, 4-(NH₂—CO)-Ph-, 2-CF₃-Ph-, 3-CF₃-Ph-, 4-CF₃-Ph-, 2-CF₃O-Ph-, 3-CF₃O-Ph-, and 4-CF₃O-Ph-);

a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl);

preferably wherein $R^{311}$ is selected from the following:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —CH₂Ph, —CH₂(2,3 or 4)F-Ph, —CH₂(2,3 or 4)Cl-Ph, —CH₂(2,3 or 4)Br-Ph, —CH₂(2,3 or 4)I-Ph, —CH₂CH₂Ph, —CH₂CH₂CH₂Ph, —CH₂CH₂CH₂CH₂Ph, —CH₂CH₂CH₂CH₂CH₂Ph, and —CH₂CH₂CH₂CH₂CH₂CH₂Ph);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F₂-Ph-, 2,(3,4,5 or 6)-Cl₂-Ph-, 2,(3,4,5 or 6)-Br₂-Ph-, 2,(3,4,5 or 6)-I₂-Ph-, 2,(3,4,5 or 6)-Me₂-Ph-, 2,(3,4,5 or 6)-Et₂-Ph-, 2,(3,4,5 or 6)-Pr₂-Ph-, 2,(3,4,5 or 6)-Bu₂-Ph-, 2,(3,4,5 or 6)-(CN)₂-Ph-, 2,(3,4,5 or 6)-(NO₂)₂-Ph-, 2,(3,4,5 or 6)-(NH₂)₂-Ph-, 2,(3,4,5 or 6)-(MeO)₂-Ph-, 2,(3,4,5 or 6)-(CF₃)₂-Ph-, 3,(4 or 5)-F₂-Ph-, 3,(4 or 5)-Cl₂-Ph-, 3,(4 or 5)-Br₂-Ph-, 3,(4 or 5)-I₂-Ph-, 3,(4 or 5)-Me₂-Ph-, 3,(4 or 5)-Et₂-Ph-, 3,(4 or 5)-Pr₂-Ph-, 3,(4 or 5)-Bu₂-Ph-, 3,(4 or 5)-(CN)₂-Ph-, 3,(4 or 5)-(NO₂)₂-Ph-, 3,(4 or 5)-(NH₂)₂-Ph-, 3,(4 or 5)-(MeO)₂-Ph-, 3,(4 or 5)-(CF₃)₂-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO₂)-Ph-, 3-(NO₂)-Ph-, 4-(NO₂)-Ph-, 2-(NH₂)-Ph-, 3-(NH₂)-Ph-, 4-(NH₂)-Ph-, 2-MeO-Ph-, 3-MeO-Ph-, 4-MeO-Ph-, 2-(NH₂—CO)-Ph-, 3-(NH₂—CO)-Ph-, 4-(NH₂—CO)-Ph-, 2-CF₃-Ph-, 3-CF₃-Ph-, 4-CF₃-Ph-, 2-CF₃O-Ph-, 3-CF₃O-Ph-, and 4-CF₃O-Ph-);

a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran- 3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).

In more typical embodiments, $R^{32}$ is selected from H or a $C_1$-$C_6$ alkyl group (such as Me, Et, Pr, i-Pr, n-Bu, i-Bu, t-Bu, pentyl and hexyl).

In more typical embodiments, $R^{33}$ is selected from H, a substituted or unsubstituted $C_1$-$C_6$ alkyl group, an $NH_2$ group or a substituted or unsubstituted $C_1$-$C_6$ amino group, a substituted or unsubstituted $C_1$-$C_6$ alkoxy group, and a nitrile group.

In some typical embodiments, the present invention provides a tryptophan-2,3-dioxygenase (TDO) and/or indoleamine-2,3-dioxygenase (IDO) inhibitor compound for use in medicine, which compound comprises the following formula:

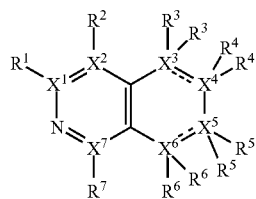

wherein $X^1$, $X^2$, and $X^7$, may be the same or different and each is independently selected from C and N; $X^3$, $X^4$, $X^5$, and $X^6$ may be the same or different and each is independently selected from C, N, O and S wherein when $X^3$ is N it has a double bond and wherein when $X^6$ is N it has a double bond; the dotted line is a bond which may be present or absent; $R^1$, $R^2$, $R^3$, $R^4$, $R^5$, $R^6$, and $R^7$ may be present or absent and may be the same or different and each is independently selected from H and a substituted or unsubstituted organic group, provided that at least one of $R^2$, $R^3$, $R^4$ and $R^6$ comprises a group Y; and provided that the number of $R^1$, $R^2$, $R^3$, $R^4$, $R^5$, $R^6$, and $R^7$ groups present is such that the respective valencies of $X^1$, $X^2$, $X^3$, $X^4$, $X^6$, and $X^7$ are maintained; and wherein Y is a group having a formula selected from the following:

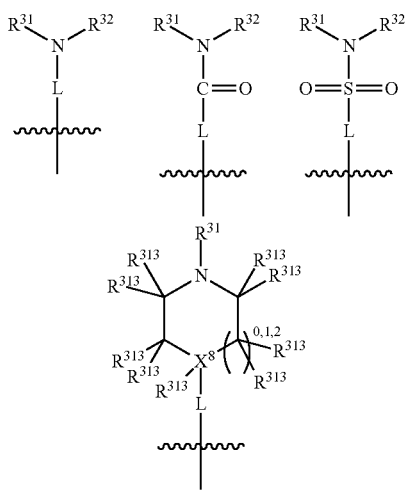

wherein L may be present or absent, and may be a substituted or unsubstituted organic linking group, and $R^{31}$ and $R^{32}$ may be the same or different and are selected from H and a substituted or unsubstituted organic group, $X^8$ is selected from C and N, and each $R^{313}$ may be the same or different and is selected from H and a substituted or unsubstituted organic group, and wherein if Y is a group of the following formula:

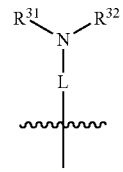

in which L is absent, $R^{32}$ is H, and $R^{31}$ comprises a carbonyl group directly bonded to the N, (or $R^{31}$ is H, and $R^{32}$ comprises a carbonyl group directly bonded to the N) then Y is a group having the following formula:

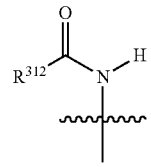

wherein $R^{312}$ is selected from any of the following:
  a substituted or unsubstituted linear or branched $C_1$-$C_6$ alkyl group (such as Me, Et, Pr, r, n-Bu, i-Bu, t-Bu, pentyl and hexyl);
  a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);
  a substituted or unsubstituted linear or branched $C_1$-$C_6$ halogenated alkyl group (such as —$CH_2$F, —$CF_3$, —$CH_2CF_3$);

an —NH$_2$ or a substituted or unsubstituted linear or branched primary secondary or tertiary C$_1$-C$_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic C$_3$-C$_8$ alkyl group (such as cyclopropyl, cyclobutyl, cyclopentyl, cyclohexyl, cycloheptyl and cyclooctyl);

a substituted or unsubstituted linear or branched C$_1$-C$_6$ alcohol group (such as —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched amino-alkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted 6 membered carbocyclic or heterocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$-00)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-, pyridin-2-yl, pyridine-3-yl, pyridin-4-yl, pyrimidin-2-yl, pyrimidin-5-yl, pyrimidin-4-yl, pyridazin-3-yl, pyridazine-4-yl);

a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein R$^{312}$ is selected from the following:

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted cyclic C$_3$-C$_8$ alkyl group (such as cyclopropyl, cyclobutyl, cyclopentyl, cyclohexyl, cycloheptyl and cyclooctyl);

a substituted or unsubstituted 6 membered carbocyclic or heterocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph-, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-, pyridin-2-yl, pyridine-3-yl, pyridin-4-yl, pyrimidin-2-yl, pyrimidin-5-yl, pyrimidin-4-yl, pyridazin-3-yl, pyridazine-4-yl);

a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

Thus, the present invention provides a TDO or IDO inhibitor compound for use in medicine, which compound comprises a formula selected from one of the following:

1 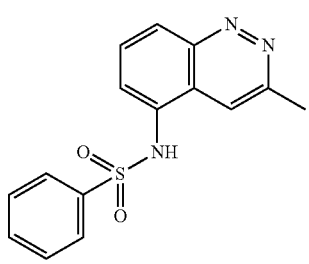
2 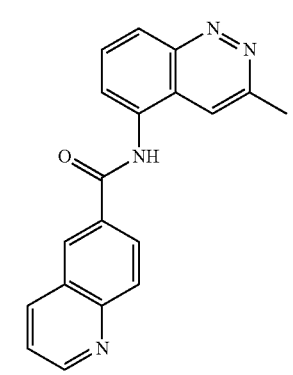
3 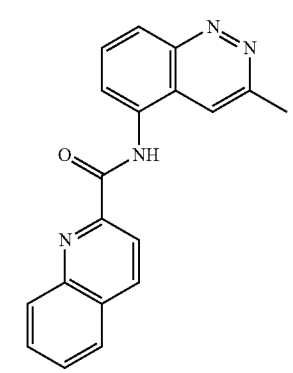
4 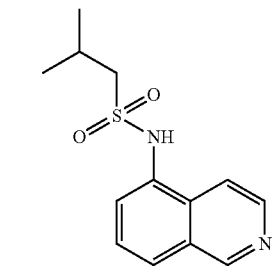
5 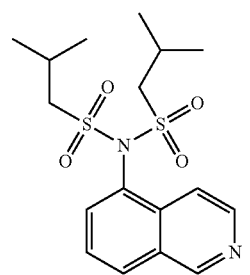
6 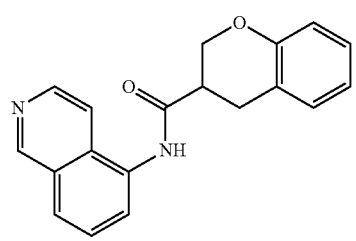
7 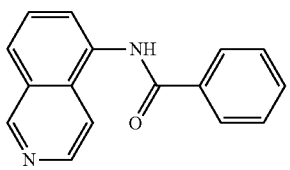
8 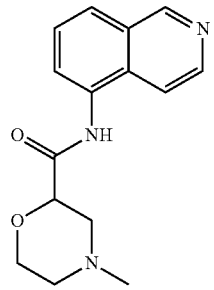
9 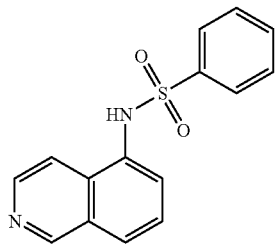
10 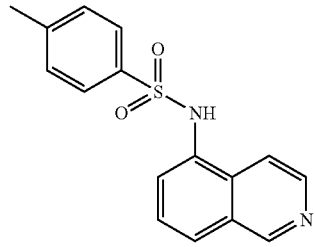
11 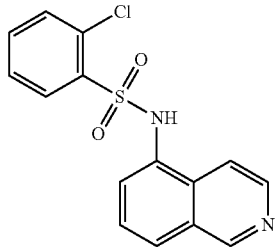

12
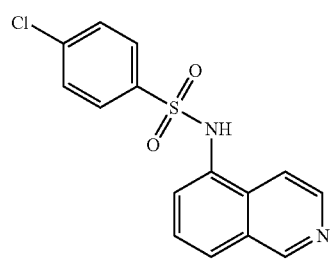
13
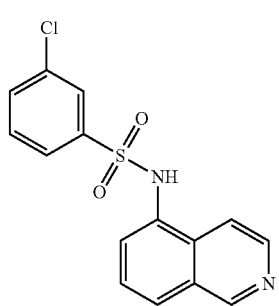
14
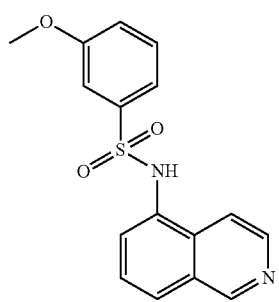
15
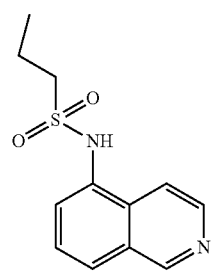
16
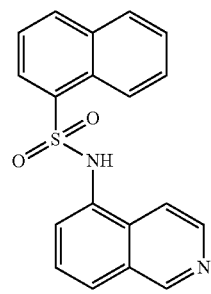
17
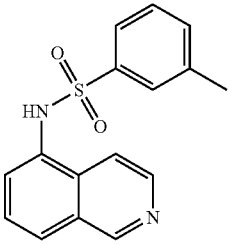
18
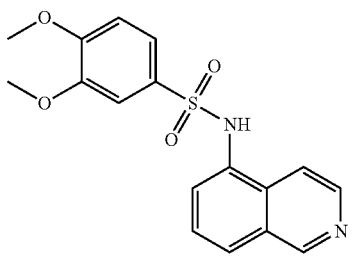
19
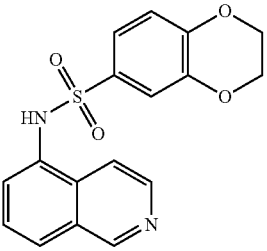
20
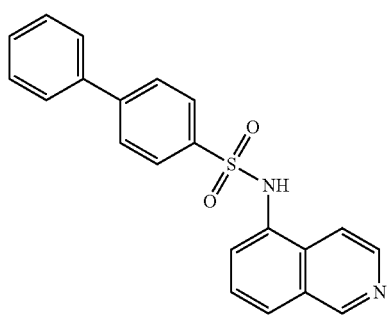
21
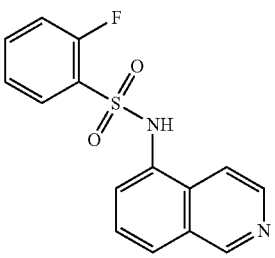
22
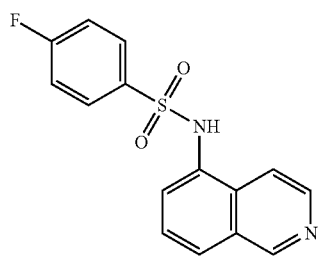

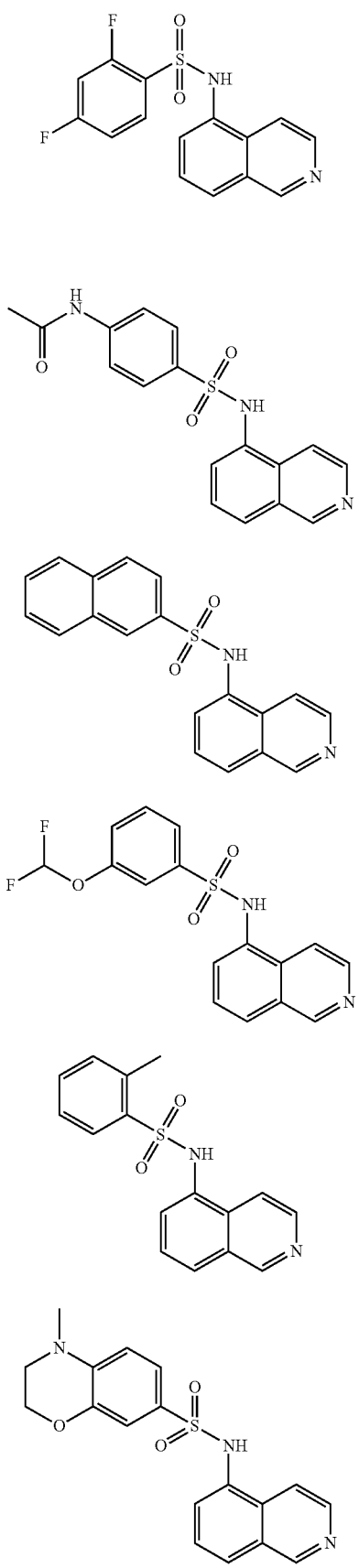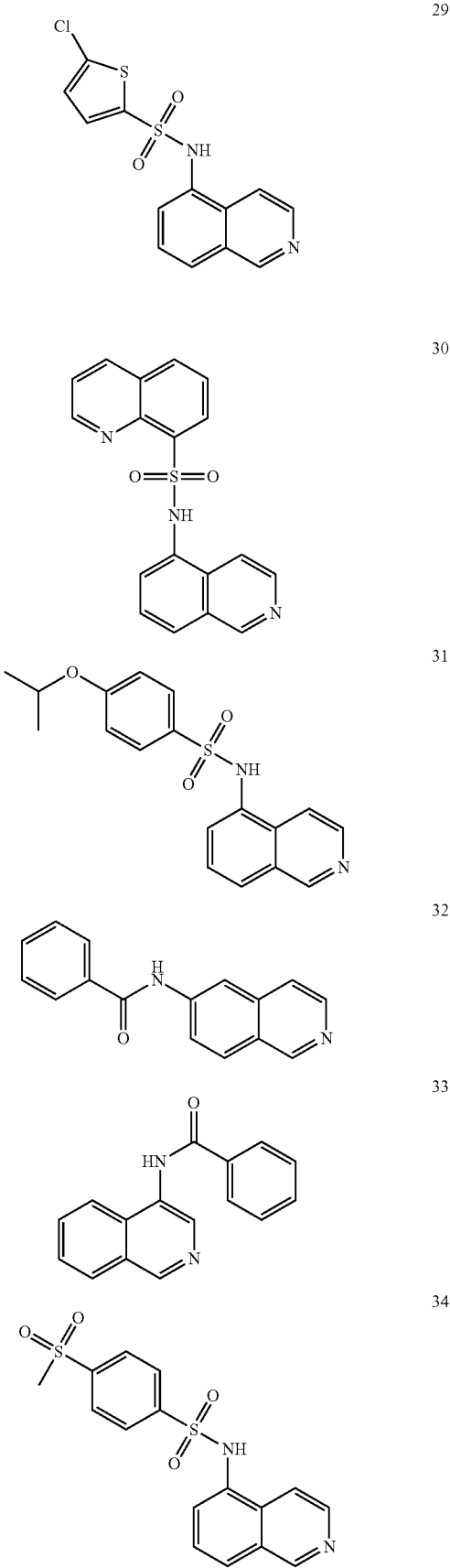

35
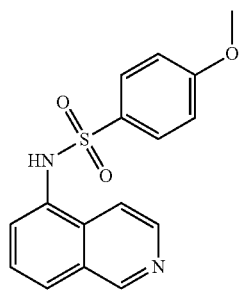
36
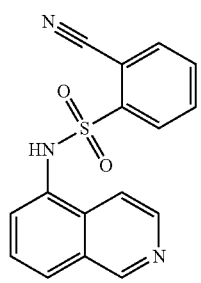
37
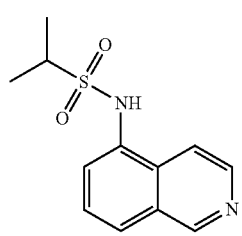
38
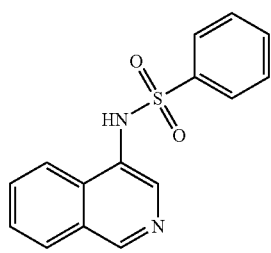
39
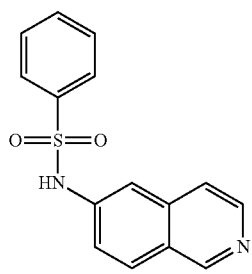
40
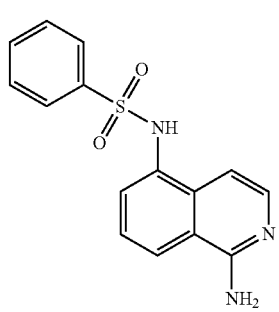
41
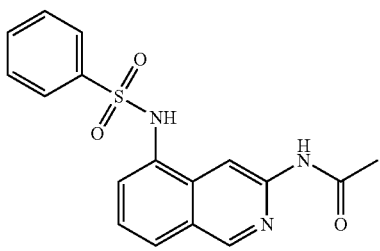
42
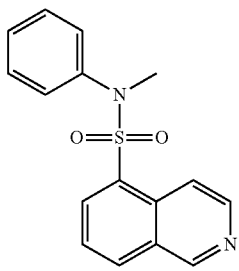
43
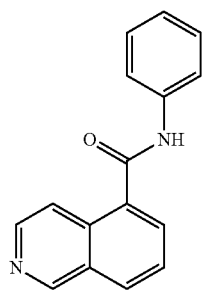
44
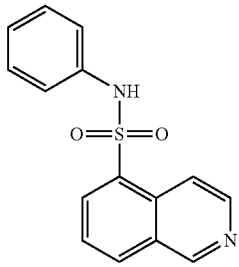
45
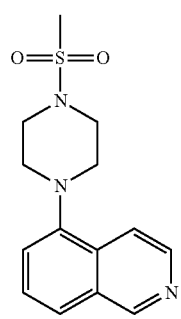

46 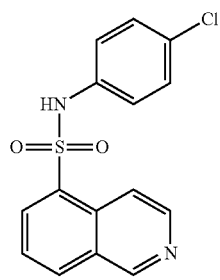
47 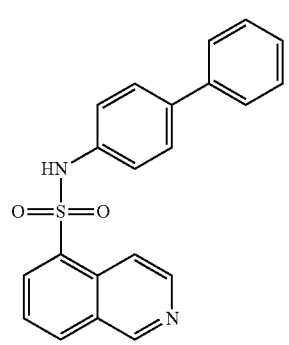
48 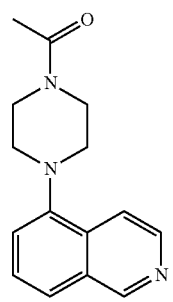
49 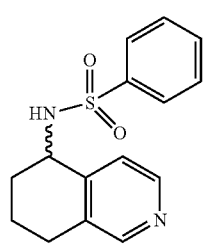
50 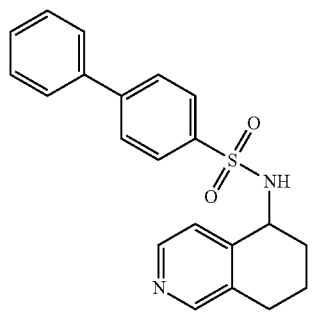
51 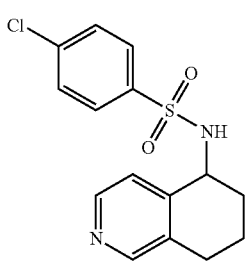
52 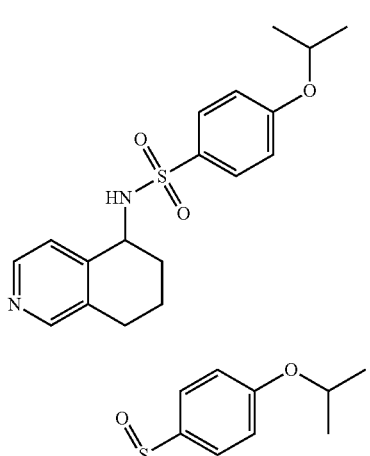
53 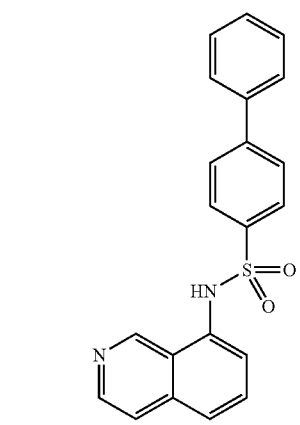
54 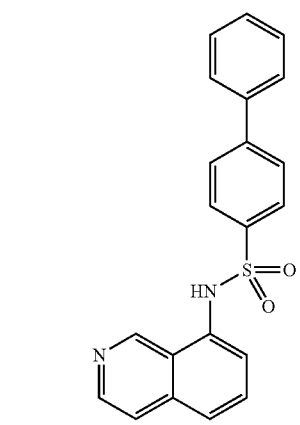
55 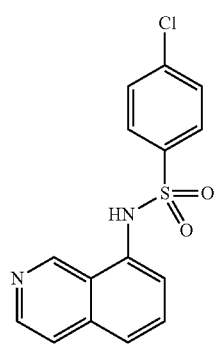

-continued

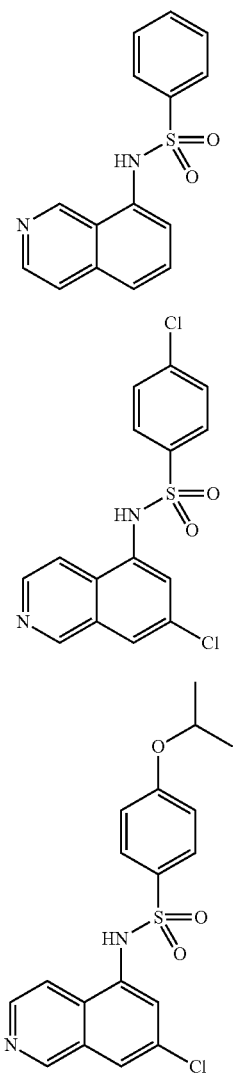

56

57

58

Typically, the above formulae (and all formulae herein) are shown in non-stereoisomeric form. For the avoidance of doubt, throughout the present disclosure a single formula is intended to represent all possible stereoisomers of a particular structure, including all possible isolated enantiomers corresponding to the formula, all possible mixtures of enantiomers corresponding to the formula, all possible mixtures of diastereomers corresponding to the formula, all possible mixtures of epimers corresponding to the formula and all possible racemic mixtures corresponding to the formula. In addition to this, the above formulae (and all formulae herein) are intended to represent all tautomeric forms equivalent to the corresponding formula.

In the context of the present invention, the medicinal use is not especially limited, provided that it is a use which is facilitated by the TDO and/or the IDO inhibitory effect of the compound. Thus, the compounds of the invention may be for use in any disease, condition or disorder that may be prevented, ameliorated or treated using a TDO and/or IDO inhibitor. Typically this comprises a disease condition and/or a disorder selected from: a cancer, an inflammatory condition, an infectious disease, a central nervous system disease or disorder, coronary heart disease, chronic renal failure, post anaesthesia cognitive dysfunction, a disease condition and/or a disorder relating to female reproductive health including contraception or abortion, and cataracts.

When the disease, condition or disorder is an inflammatory disease, condition or disorder, it is not especially limited, provided that the disease, condition or disorder is one which may be treated, prevented or ameliorated by using a TDO and/or IDO inhibitor. However, typically the inflammatory condition is a condition relating to immune B cell, T cell, dendritic cell, natural killer cell, macrophage, and/or neutrophil dysregulation.

When the disease, condition or disorder is a cancer, it is not especially limited, provided that the cancer is one which may be treated, prevented or ameliorated by using a TDO and/or IDO inhibitor. Thus the cancer may be a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, oesophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma, Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, Proteus syndrome, and Proteus-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelomonocytic leukaemia, Hodgkin lymphoma, non-Hodgkin lymphoma, mantle lymphoma, follicular lymphoma, primary effusion lymphoma, AIDS-related lymphoma, Hodgkin lymphoma, diffuse B cell lymphoma, Burkitt lymphoma, and cutaneous T-cell lymphoma). However, when the compound is an IDO inhibitor, typically (but not exclusively) the cancer is a cancer selected from acute myeloid leukemia (AML), a small-cell lung cancer, a melanoma, an ovarian cancer, a colorectal cancer, a pancreatic cancer, an endometrial cancer, and a skin papilloma. When the compound is a TDO inhibitor, typically (but not exclusively) the cancer is a cancer selected from a glioma, and a hepatocellular carcinoma.

When the disease is an infectious disease, it is not especially limited, provided that the disease is one which may be treated, prevented or ameliorated by using a TDO and/or IDO inhibitor. However, typically the infectious disease is selected from a bacterial infection and a viral infection, preferably a gut infection, sepsis, and sepsis induced hypotension.

When the disease, condition or disorder is a central nervous system disease, condition or disorder, it is not especially limited, provided that the disease, condition or disorder is one which may be treated, prevented or ameliorated by using a TDO and/or IDO inhibitor. However, the central nervous system disease, condition or disorder is typically selected from amyotrophic lateral sclerosis (AML), Huntington's disease, Alzheimer's disease, pain, a psychiatric disorder, multiple sclerosis, Parkinson's disease, and HIV related neurocognitive decline.

When the disease, condition or disorder is one relating to female reproductive health, it is not especially limited provided that the disease, condition or disorder is one which may be treated, prevented or ameliorated by using a TDO and/or IDO inhibitor. In typical embodiments the disease, condition or disorder is selected from gynaecological disorders such as endometriosis. Conditions relating to female reproductive health that are included in the invention include contraception and abortion such that the compounds of the invention may be used as a contraceptive and/or abortive agent.

The present invention also provides a pharmaceutical composition comprising a compound as defined above. Whilst the pharmaceutical composition is not especially limited, typically the composition further comprises a pharmaceutically acceptable additive and/or excipient. In the pharmaceutical composition, the compound as defined above may be present in the form described above, but may alternatively be in a form suitable for improving bioavailability, solubility, and/or activity, and/or may be in a form suitable for improving formulation. Thus, the compound may be in the form of a pharmaceutically acceptable salt, hydrate, acid, ester, or other alternative suitable form. Typically, the composition is for treating a disease, condition or disorder as defined above.

In some embodiments the pharmaceutical composition is a composition for treating a cancer, further comprising a further agent for treating cancer. The further agent for treating cancer is not especially limited, provided that it affords some utility for cancer treatment. However, typically the further agent for treating cancer is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors. An immunotherapeutic agent may consist of but is not limited to an anti-tumour vaccine, an oncolytic virus, an immune stimulatory antibody such as anti-CTLA4, anti-PD1, anti-PDL-1, anti-OX40, anti-41BB, anti-CD27, anti-CD40, anti-LAGS, anti-TIM3, and anti-GITR, a novel adjuvant, a peptide, a cytokine, a chimeric antigen receptor T cell therapy (CAR-T), a small molecule immune modulator, tumour microenvironment modulators, and anti-angiogenic agents.

In still further embodiments the invention provides a pharmaceutical kit for treating a cancer, which pharmaceutical kit comprises:
(a) a compound as defined above; and
(b) a further agent for treating cancer; preferably wherein the further agent for treating cancer is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors;
wherein the compound and the further agent are suitable for administration simultaneously, sequentially or separately.

Further provided by the invention is a method of treating a disease and/or a condition and/or a disorder, which method comprises administering to a patient (or subject) a compound, or a composition, or a kit as defined above. The method is typically a method for treating any disease condition or disorder mentioned herein. In typical embodiments, the method is a method for treating a cancer. Preferably such a method comprises administering to a patient (or subject) a compound or a composition as defined above and a further agent for treating cancer as defined above. The compound or composition and the further agent may administered simultaneously, sequentially or separately, depending upon the agents and patients involved, and the type of cancer indicated.

Typically, in all embodiments of the invention, both above and below, the patient (or subject) is an animal, typically a mammal, and more typically a human.

In addition to compounds for use in medicine, the present invention, and in particular the synthetic method, provides compounds that were not previously known, such compounds comprising a formula selected from one of the following:

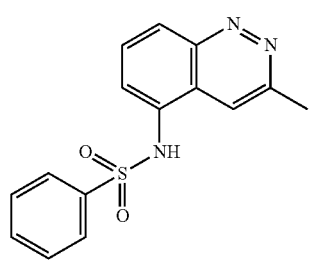

1

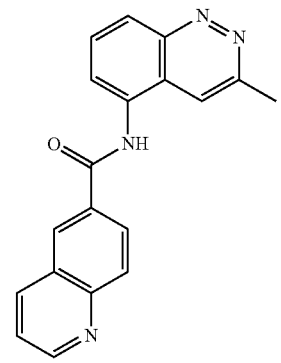

2

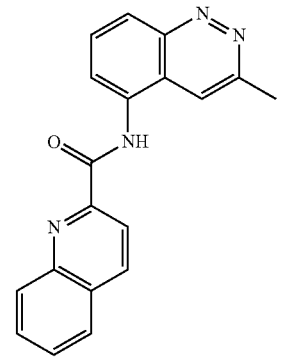

3

| | |
|---|---|
| 4 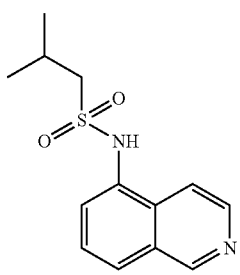 | 17 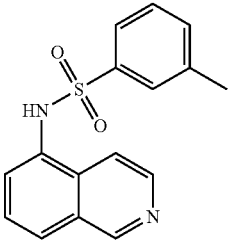 |
| 5 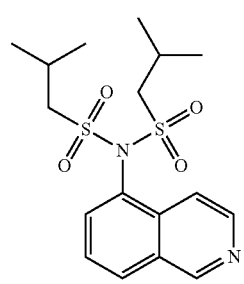 | 18 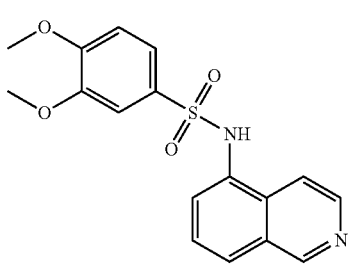 |
| 11 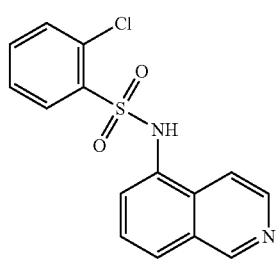 | 19 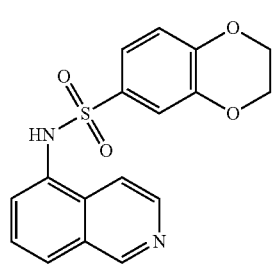 |
| 13 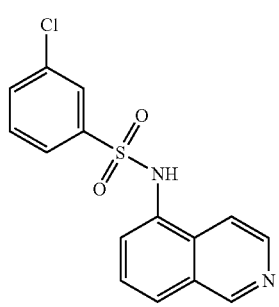 | 23 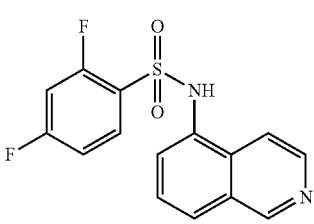 |
| | 25 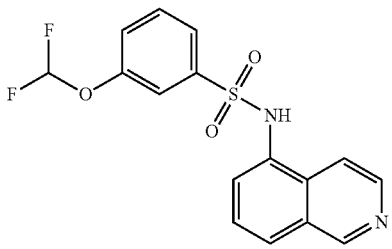 |
| 14 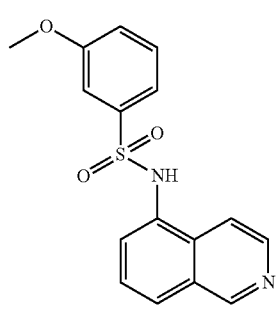 | 28 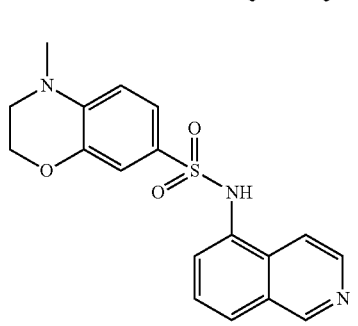 |

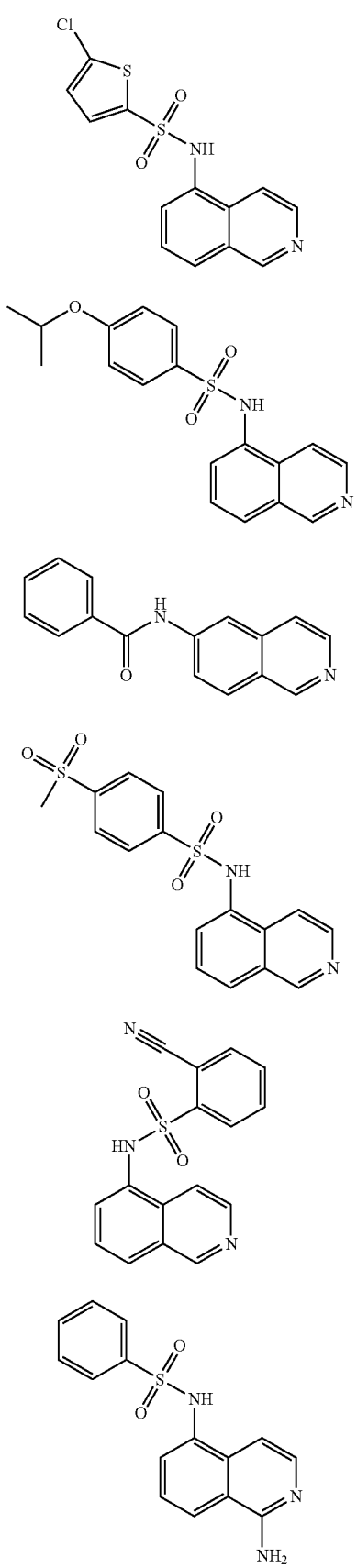
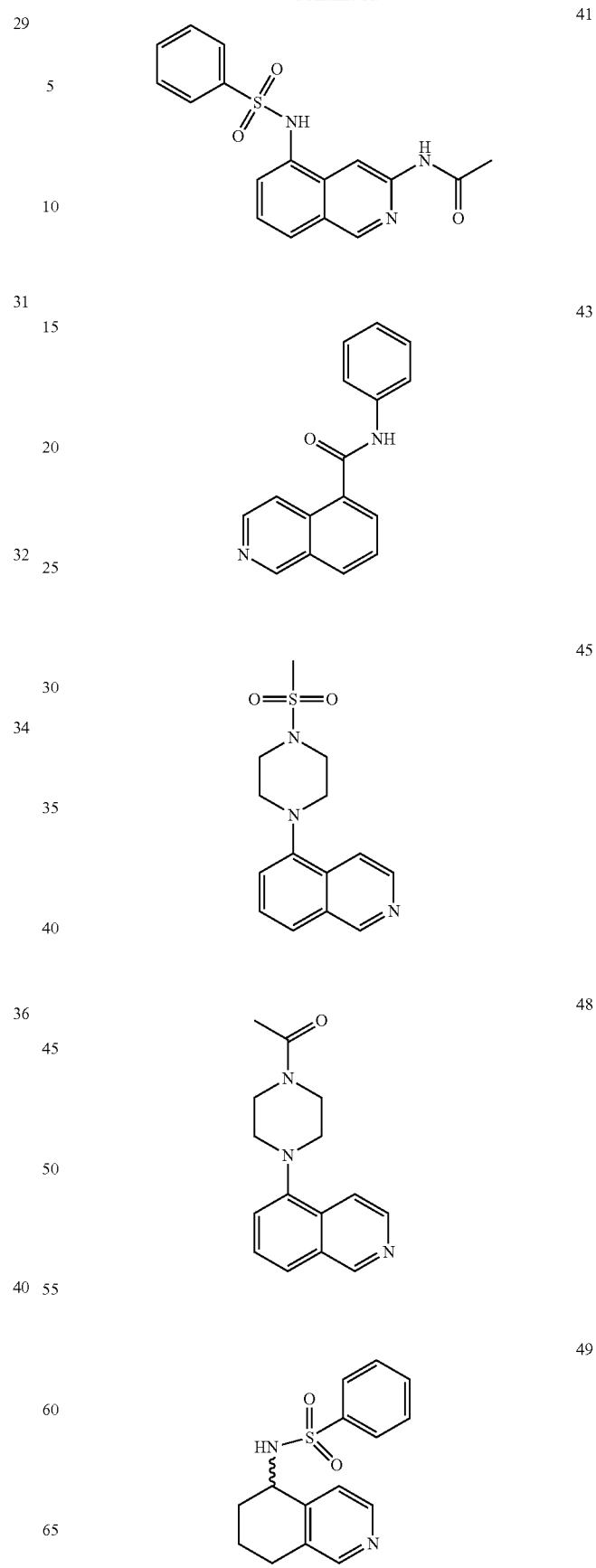

50

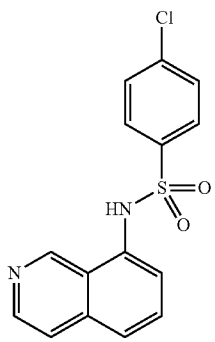

55

51

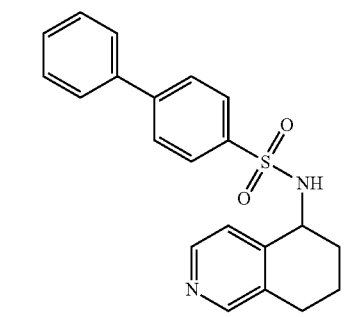

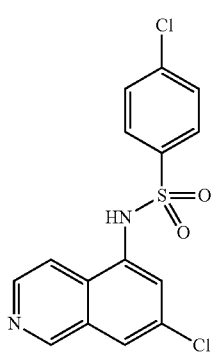

57

52

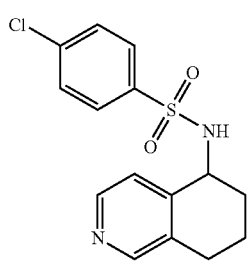

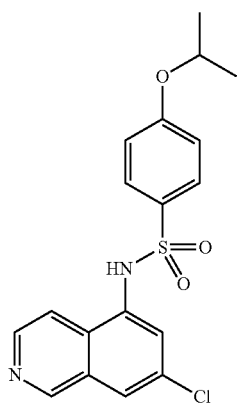

58

53

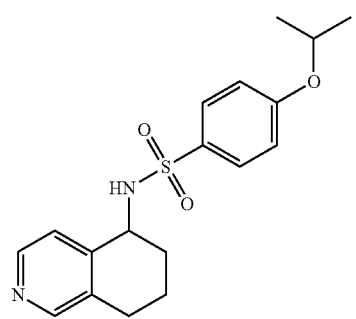

54

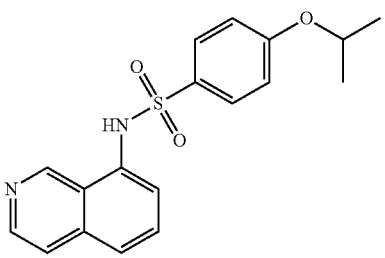

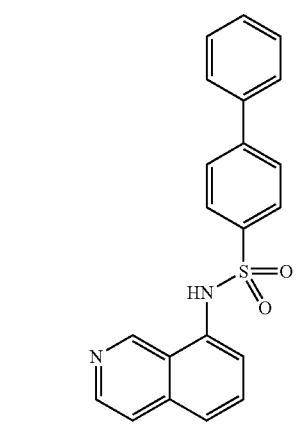

Typically, the above formulae (and all formulae herein) are shown in non-stereoisomeric form. For the avoidance of doubt, throughout the present disclosure a single formula is intended to represent all possible stereoisomers of a particular structure, including all possible isolated enantiomers corresponding to the formula, all possible mixtures of enantiomers corresponding to the formula, all possible mixtures of diastereomers corresponding to the formula, all possible mixtures of epimers corresponding to the formula and all possible racemic mixtures corresponding to the formula. In addition to this, the above formulae (and all formulae herein) are intended to represent all tautomeric forms equivalent to the corresponding formula.

Further provided by the invention is a method of synthesis of novel compounds, as defined above, which method comprises a step of reacting a compound having one of the following formulae:

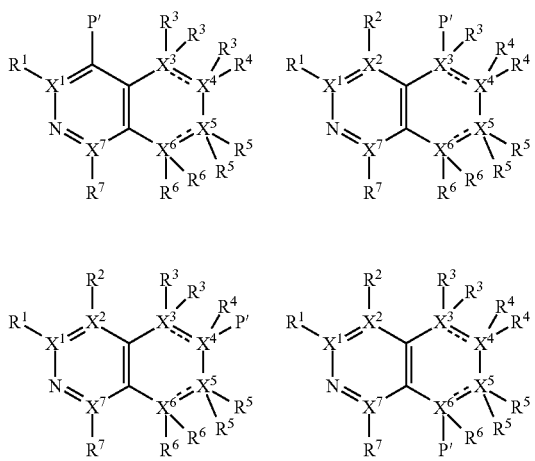

wherein the groups R and X are as defined anywhere herein; the dotted lines are bonds which may be present or absent; and wherein P' is a precursor group to group Y, in order to form the group Y from P' and produce a compound having one of the following formulae:

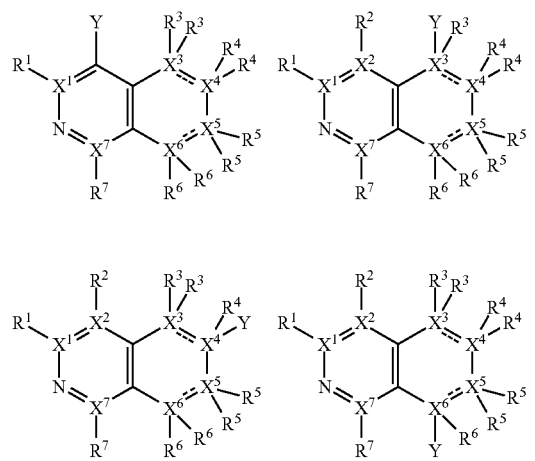

The skilled person may select the type of reagents, and the reaction conditions, with reference to known synthesis techniques. In some embodiments, the method comprises one or more additional substitution steps. Exemplary syntheses are shown in the Examples.

The invention will now be described in more detail, by way of example only, with reference to the following specific embodiments.

EXAMPLES

Example 1

Methods of Synthesis

The following three syntheses are representative exemplary methods by which the compounds of the present invention may be synthesised:

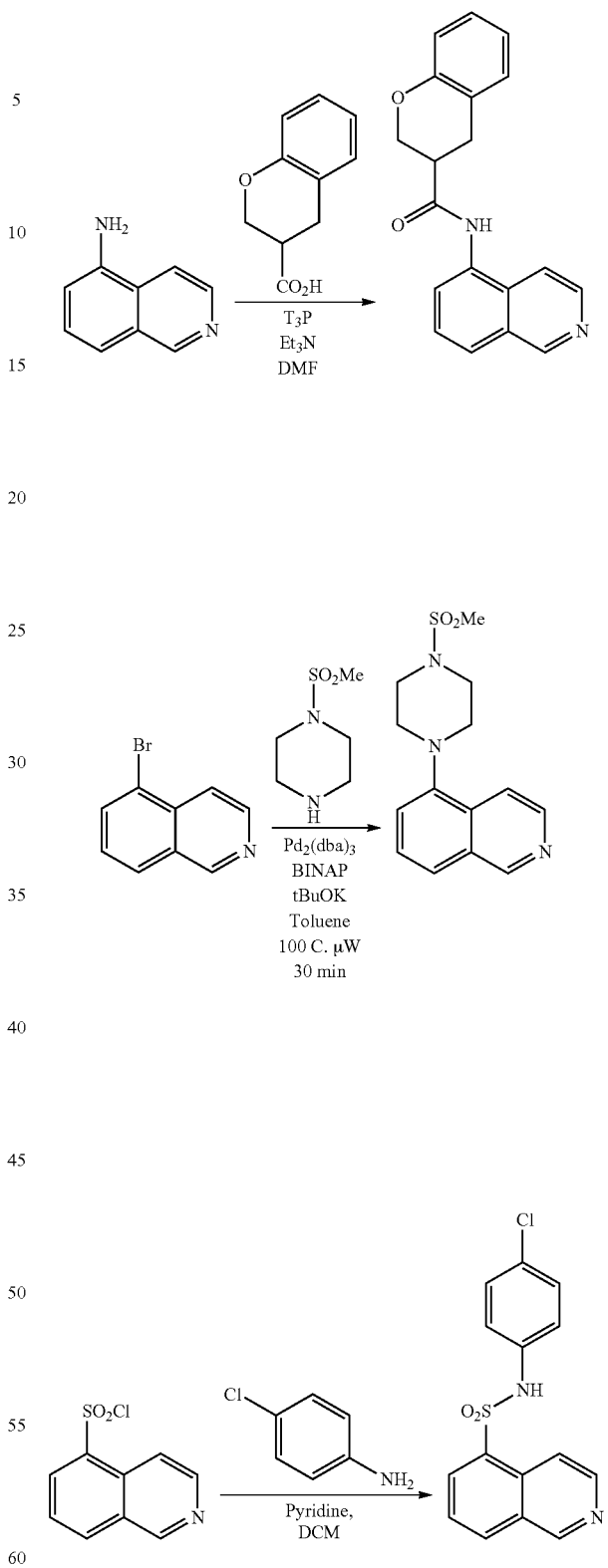

All three syntheses may be performed using reagents and reaction conditions suitable for similar reactions known in the field. All the compounds of the present invention may be produced by employing analogous syntheses.

Some specific syntheses of compounds of the present invention are set out in the following.

Synthesis of Compound 45

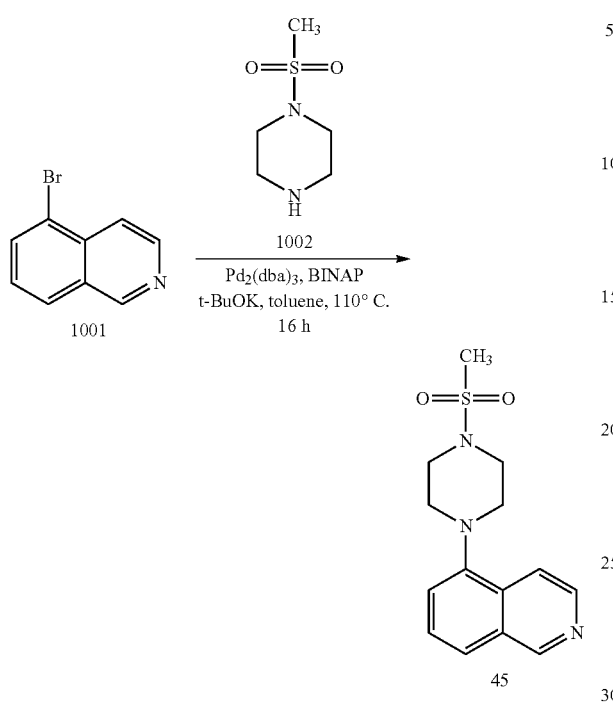

Reagents were purchased from the commercial sources and were used as received. $^1$H NMR spectra were obtained on a Bruker AVANCE 300 spectrometer at 300 MHz and a Bruker AVANCE 400 spectrometer at 400 MHz with tetramethylsilane used as an internal reference. Thin-layer chromatography (TLC) was performed using Whatman No. 4500-101 (Diamond No. MK6F silica-gel 60 Å) plates. Visualization of TLC plates was performed using UV light (254 nm). The mass spectra were obtained on a Finnigan LCQ-DUO spectrometer using electrospray ionization. HPLC analyses were performed on an Agilent 1100 Series instrument. Impurities are expressed as % AUC by HPLC and are non-validated.

Preparation of 5-(4-(methylsulfonyl)piperazin-1-yl)isoquinoline (45)

A stirred solution of 1001 (100 mg, 0.48 mmol) in toluene (1.0 mL) was charged with 1002 (78 mg, 0.48 mmol), t-BuOK (107 mg, 0.96 mmol) and the mixture was purged with argon for 20 min. Pd$_2$(dba)$_3$ (21 mg, 0.02 mmol) and BINAP (22 mg, 0.03 mmol) were added into this mixture and refluxed at 110° C. for 16 h. The mixture was cooled to room temperature and concentrated under reduced pressure. The resultant dark brown slurry was filtered through Celite® pad and pad was washed with ethyl acetate (30 mL). The solvent was concentrated in vacuo to give a dark brown residue. This residue was further purified by Combiflash column chromatography using 12 g Redisep® column (hexane/EtOAc, 1:1) to afford 45 (20 mg, 14%) as an off-white solid.

MS (MM) m/z 292 [M+H]$^+$;
HPLC: 95.9%, Eclipse XDB C-18, 220 nm;
$^1$H NMR (300 MHz, DMSO-d$_6$): δ 9.29 (s, 1H), 8.52 (d, J=5.1 Hz, 1H), 7.92 (d, J=4.8 Hz, 1H), 7.82 (d, J=7.5 Hz, 1H), 7.62 (t, J=7.2 Hz, 1H), 7.40 (d, J=6.9 Hz, 1H), 3.42 (bs, 4H), 3.14 (bs, 4H), 2.99 (s, 3H).

Synthesis of Compound 28

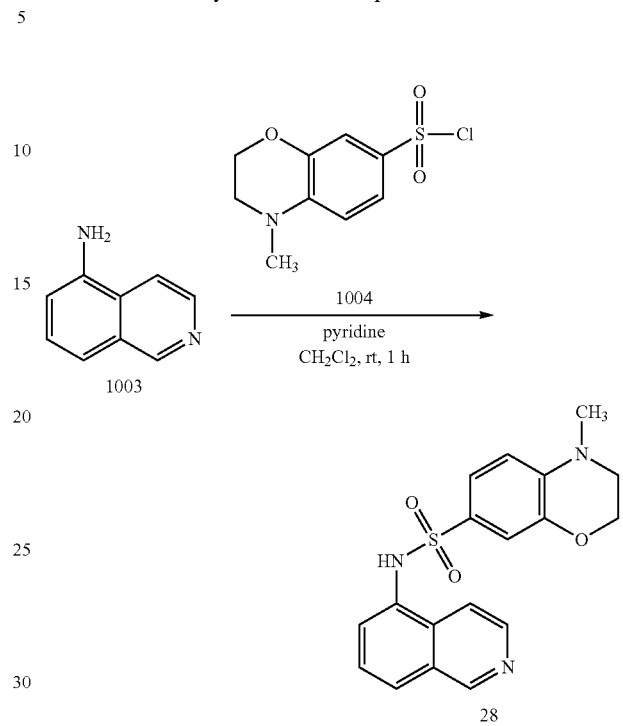

A solution 1003 (75 mg, 0.29 mmol) in CH$_2$Cl$_2$ (5 mL) was treated with pyridine (0.1 mL) followed by 1004 (42 mg, 0.29 mmol) at 0° C. After being stirred at room temperature for 1 h, the reaction mixture was diluted with CH$_2$Cl$_2$ (15 mL), washed with water (5 mL) and brine (5 mL). The organic phase was separated, dried over anhydrous Na$_2$SO$_4$, filtered and concentrated in vacuo to give a brown solid residue. This residue was further purified by Combiflash column chromatography using 4 g Redisep® column (hexane/EtOAc, 1:1) to afford 28 (35 mg, 33%) as an off-white solid.

MS (MM) m/z 356 [M+H]$^+$;
HPLC: 99%, Symmetry C-18 column, 220 nm;
$^1$H NMR (300 MHz, DMSO-d$_6$): δ 10.3 (s, 1H), 9.48 (s, 1H), 8.50 (d, J=6.3 Hz, 1H), 8.09 (t, J=9.0 Hz, 2H), 7.72 (t, J=8.1 Hz, 1H), 7.58 (d, J=7.5 Hz, 1H), 6.86-6.84 (m, J=2H), 6.69 (d, J=8.4 Hz, 1H), 4.23 (t, J=3.9 Hz, 2H), 3.21 (t, J=3.9 Hz, 2H), 2.69 (s, 3H)

Synthesis of Compound 52

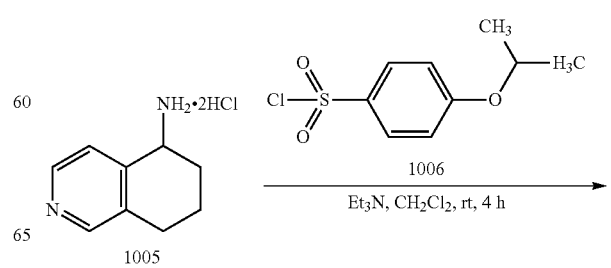

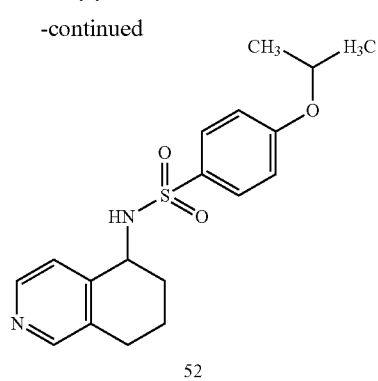

52

A solution of 1005 (100 mg, 0.45 mmol) in $CH_2Cl_2$ (5 mL) was treated with $Et_3N$ (0.25 mL, 1.8 mmol) followed by 1006 (106 mg, 0.45 mmol) at 0° C. After being stirred at room temperature for 4 h, the reaction mixture was diluted with $CH_2Cl_2$ (15 mL), washed with water (5 mL) and brine (5 mL). The organic phase was separated, dried over anhydrous $Na_2SO_4$, filtered and concentrated in vacuo to give a yellow color solid. This residue was further purified by preparative TLC (hexanes/EtOAc, 1:1) to afford 52 (20 mg, 13%) as a light yellow solid.

MS (MM) m/z 347 [M+H]$^+$;

HPLC: 97.5%, Eclipse XBD C18, 254 nm;

$^1$H NMR (400 MHz, DMSO-$d_6$): δ 8.28 (s, 1 H), 8.27 (d, J=3.6 Hz, 1H), 8.02 (d, J=8.8 Hz, 1H), 7.78 (d, J=8.8 Hz, 2H), 7.11-7.09 (m, 3 H), 4.78-4.72 (m, 1 H), 4.28 (q, J=8.4 Hz, 1 H), 2.66-2.62 (m, 2 H), 1.79-1.76 (m, 1 H), 1.63-1.59 (m, 2 H), 1.54-1.49 (m, 1 H), 1.30 (d, J=6.0 Hz, 6 H)

Example 2

Assays

Exemplary compounds of the invention were prepared, and tested to determine their effect as TDO and/or IDO inhibitors. Two different assays were employed: 1. a cell-based assay for detecting the effect of test compounds on kynurenine production in two different cancer cell types. This assay utilised cancer cells which expressed either TDO or IDO and as such was used as a means of testing compound activity at these two enzymes in a cell-based context. 2. a TDO and IDO biochemical coupled assay which utilised recombinantly produced and purified TDO and IDO enzymes in combination with the enzyme formamidase. This coupled enzyme system allowed conversion of N-formylkynurenine produced by TDO or IDO activity to kynurenine which was then quantified by fluorescence following addition of Erhlich's Reagent The protocols for these are set out below.

Cell Based Assay for Detection of Kynurenine Produced by TDO and/or IDO

A172 (human glioblastoma) and SKOV3 (human ovarian adenocarcinoma) cells were seeded in a 96 well plate at 30,000 or 40,000 cells per well respectively in phenol red-free RPMI supplemented with 10% FCS, 2 mM L-glutamine and 500 μM L-tryptophan. IDO expression was induced in the SKOV3 cells by the addition of 500 ng/ml IFN-γ. Cells were incubated at 37° C. with or without the addition of test compound. After 48 hours, the cells were removed by centrifugation and Erhlich's reagent was added to the supernatant. The Erhlich's reagent was incubated for 5 minutes before the absorbance was read at 490 nM.

TDO and IDO Biochemical Coupled Assay

Recombinant human IDO or TDO was incubated in 50 mM KPO4 (pH 7.0), 0.5 mM EGTA, 0.5 mM EDTA, 0.05% Triton™ X100, 20 mM ascorbate, 10 μM methylene blue, 500 U/ml catalase, 50 μg/ml KynB (kynurenine formamidase). TDO assays were carried out in the presence of 330 μM L-tryptophan, while IDO assays had the addition of 45 μM L-tryptophan. After incubation for 17 minutes at room temperature the reactions were stopped by the addition of Erhlich's reagent and incubated at room temperature for 5 minutes before the fluorescence was read (Ex475, Em530).

The pIC50 values for a variety of test compounds are shown in Table 1 and Table 2.

TABLE 1 pIC50 values for Kynurenine cell-based assays determined for test compounds

| Compound | A172 Kynurenine cell based assay pIC50 | SKOV3 Kynurenine cell based assay pIC50 |
|---|---|---|
| 1 | + | + |
| 2 | + | + |
| 3 | + | +/− |
| 4 | + | +/− |
| 5 | +/− | + |
| 6 | + | ++ |
| 7 | +/− | + |
| 8 | ++ | ++ |
| 9 | +++ | ++ |
| 10 | +/− | ++ |
| 11 | ++ | ++ |
| 12 | ++ | ++ |
| 13 | ++ | ++ |
| 14 | +++ | ++ |
| 15 | ++ | +/− |
| 16 | ++ | ++ |
| 17 | +++ | ++ |
| 18 | +/− | + |
| 19 | +++ | +++ |
| 20 | +++ | +++ |
| 21 | ++ | ++ |
| 22 | +++ | + |
| 23 | +/− | + |
| 24 | +/− | ++ |
| 25 | +++ | +++ |
| 26 | +++ | ++ |
| 27 | +++ | ++ |
| 28 | +++ | ++ |
| 29 | ++ | ++ |
| 30 | +/− | + |
| 31 | +/− | +++ |
| 32 | +/− | + |
| 33 | +/− | + |
| 34 | +/− | + |
| 35 | +++ | ++ |
| 36 | +/− | + |
| 37 | + | +/− |
| 38 | + | + |
| 39 | +/− | + |
| 40 | + | + |
| 41 | +/− | + |
| 42 | + | + |
| 43 | +/− | + |
| 44 | + | ++ |
| 45 | +/− | + |
| 46 | + | ++ |
| 47 | ++ | ++ |
| 48 | +/− | + |
| 49 | +/− | + |
| 50 | +/− | +++ |
| 51 | +/− | ++ |
| 52 | +/− | +++ |
| 53 | + | + |
| 54 | + | + |

TABLE 1-continued pIC50 values for Kynurenine cell-based assays determined for test compounds

| Compound | A172 Kynurenine cell based assay pIC50 | SKOV3 Kynurenine cell based assay pIC50 |
|---|---|---|
| 55 | + | ++ |
| 56 | +/− | + |
| 57 | +/− | ++ |
| 58 | +/− | ++ |

Key:
+++ = $pIC_{50} \geq 5.50$
++ = $pIC_{50}$ 4.50-5.49
+ = $pIC_{50}$ 4.00-4.49
+/− = $pIC_{50}$ <4.00

TABLE 2 pIC50 values for IDO and TDO inhibition determined for test compounds

| Compound | hIDO biochemical assay pIC50 | hTDO biochemical assay pIC50 |
|---|---|---|
| 1 | ++ | ++ |
| 2 | +/− | ++ |
| 3 | +/− | + |
| 4 | ++ | +++ |
| 6 | +++ | +++ |
| 9 | ++ | ++ |
| 14 | ++ | +− |
| 16 | ++ | + |
| 56 | + | +/− |
| 57 | + | +/− |
| 58 | + | +/− |

Key:
+++ = $pIC_{50} \geq 5.50$
++ = $pIC_{50}$ 4.50-5.49
+ = $pIC_{50}$ 4.00-4.49
+/− = $pIC_{50}$ <4.00

The Table shows that a large number of the test compounds show strong TDO and IDO inhibitory function.

The invention claimed is:
1. A compound having one of the following formulae, or a pharmaceutically acceptable salt thereof:

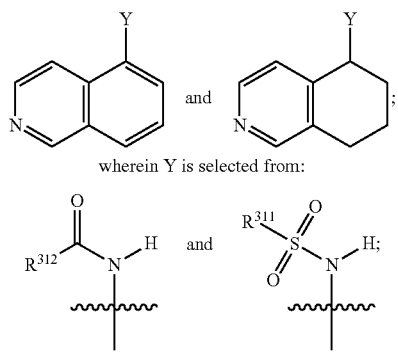

wherein Y is selected from:

$R^{311}$ is selected from:
a substituted or unsubstituted linear or branched $C_1$-$C_6$ alkyl group selected from Me, Et, Pr, i-Pr, n-Bu, i-Bu, t-Bu, pentyl and hexyl;
a substituted or unsubstituted linear or branched $C_1$-$C_6$ alkyl-aryl group —$CH_2Ph$, —$CH_2(2,3$ or $4)F$-$Ph$, —$CH_2(2,3$ or $4)Cl$-$Ph$, —$CH_2(2,3$ or $4)Br$-$Ph$, —$CH_2(2,3$ or $4)I$-$Ph$, —$CH_2CH_2Ph$, —$CH_2CH_2CH_2Ph$, —$CH_2CH_2CH_2CH_2Ph$, —$CH_2CH_2CH_2CH_2CH_2Ph$, and —$CH_2CH_2CH_2CH_2CH_2CH_2Ph$;
a substituted or unsubstituted linear or branched $C_1$-$C_6$ halogenated alkyl group selected from —$CH_2F$, —$CF_3$, —$CH_2CF_3$;
an —$NH_2$ or a substituted or unsubstituted linear or branched primary secondary or tertiary $C_1$-$C_6$ amine group selected from —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt;
a substituted or unsubstituted amino-aryl group selected from —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)$F_2$-Ph, —NH-2,(3,4,5 or 6)$Cl_2$-Ph, —NH-2,(3,4,5 or 6)$Br_2$-Ph, —NH-2,(3,4,5 or 6)$I_2$-Ph, —NH-2,(3,4,5 or 6)$Me_2$-Ph, —NH-2,(3,4,5 or 6)$Et_2$-Ph, —NH-2,(3,4,5, or 6)$Pr_2$-Ph, and —NH-2,(3,4,5 or 6)$Bu_2$-Ph;
a substituted or unsubstituted cyclic amine or amido group selected from pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl;
a substituted or unsubstituted cyclic $C_3$-$C_8$ alkyl group selected from cyclopropyl, cyclobutyl, cyclopentyl, cyclohexyl, cycloheptyl and cyclooctyl;
a substituted or unsubstituted linear or branched $C_1$-$C_6$ alcohol group selected from —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, and —$CH_2CH_2CH_2CH_2CH_2CH_2OH$;
a substituted or unsubstituted linear or branched $C_1$-$C_7$ amino carbonyl group selected from —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, and —NMe-CO-Ph;
a substituted or unsubstituted linear or branched $C_1$-$C_7$ alkoxy or aryloxy group selected from —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —O-Ph, —O—$CH_2$-Ph, —O—$CH_2$-(2,3 or 4)-F-Ph, —O—$CH_2$-(2,3 or 4)-Cl-Ph, —$CH_2OMe$, —$CH_2OEt$, —$CH_2OPr$, —$CH_2OBu$, —$CH_2CH_2OMe$, —$CH_2CH_2CH_2OMe$, —$CH_2CH_2CH_2CH_2OMe$, and —$CH_2CH_2CH_2CH_2CH_2OMe$;
a substituted or unsubstituted linear or branched amino-alkoxy group selected from —$OCH_2CH_2NH_2$, —$OCH_2CH_2NHMe$, —$OCH_2CH_2NMe_2$, —$OCH_2CH_2NREt$, and —$OCH_2CH_2NEt_2$;
a substituted or unsubstituted aminosulphonyl group selected from —$NHSO_2Me$, —$NHSO_2Et$, —NHSO$_2$Pr, —NHSO$_2$iPr, —NHSO$_2$Ph, —NHSO$_2$-(2,3 or 4)-F-Ph, —NHSO$_2$-cyclopropyl, and —NHSO$_2$CH$_2$CH$_2$OCH$_3$;

a substituted or unsubstituted aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-; and 4-CF$_3$O-Ph-; and a saturated or unsaturated, substituted or unsubstituted, heterocyclic group selected from pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl; and R$^{312}$ is selected from:

a substituted or unsubstituted linear or branched C$_1$-C$_6$ alkyl group selected from Me, Et, Pr, i-Pr, n-Bu, i-Bu, t-Bu, pentyl and hexyl;

a substituted or unsubstituted linear or branched C$_1$-C$_6$ alkyl-aryl group selected from —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph;

a substituted or unsubstituted linear or branched C$_1$-C$_6$ halogenated alkyl group selected from —CH$_2$F, —CF$_3$, —CH$_2$CF$_3$;

an —NH$_2$ or a substituted or unsubstituted linear or branched primary secondary or tertiary C$_1$-C$_6$ amine group selected from —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt;

a substituted or unsubstituted amino-aryl group selected from —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, and —NH-2,(3,4,5 or 6)Bu$_2$-Ph;

a substituted or unsubstituted cyclic amine or amido group selected from pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl;

a substituted or unsubstituted cyclic C$_3$-C$_8$ alkyl group selected from cyclopropyl, cyclobutyl, cyclopentyl, cyclohexyl, cycloheptyl and cyclooctyl;

a substituted or unsubstituted linear or branched C$_1$-C$_6$ alcohol group selected from —CH$_2$OH, —CH$_2$CH$_2$OH, —CH$_2$CH$_2$OH, —CH$_2$CH$_2$CH$_2$CH$_2$OH, —CH$_2$CH$_2$CH$_2$CH$_2$CH$_2$OH, and —CH$_2$CH$_2$CH$_2$CH$_2$CH$_2$CH$_2$OH;

a substituted or unsubstituted linear or branched C$_1$-C$_7$ amino carbonyl group selected from —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, and —NMe-CO-Ph;

a substituted or unsubstituted linear or branched C$_1$-C$_7$ alkoxy or aryloxy group selected from —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe;

a substituted or unsubstituted linear or branched aminoalkoxy group selected from —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted aminosulphonyl group selected from —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$;

a substituted or unsubstituted 6 membered carbocyclic or heterocyclic aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-, pyridin-2-yl, pyridine-3-yl, pyridin-4-yl, pyrimidin-2-yl, pyrimidin-5-yl, pyrimidin-4-yl, pyridazin-3-yl, pyridazine-4-yl; and a substituted or unsubstituted saturated heterocyclic group selected from piperidin-2-yl, piperidin-3-yl, piperidin-4-yl, tetrahydrofuran-2-yl, and tetrahydrofuran-3-yl, tetrahydropyran-2-yl, tetrahydropyran-3-yl, and tetrahydropyran-4-yl.

2. The compound according to claim 1, or a pharmaceutically acceptable salt thereof, wherein R$^{312}$ is selected from:

a substituted or unsubstituted linear or branched C$_1$-C$_6$ alkyl-aryl group selected from —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph;

a substituted or unsubstituted cyclic C$_3$-C$_8$ alkyl group (such as cyclopropyl, cyclobutyl, cyclopentyl, cyclohexyl, cycloheptyl and cyclooctyl;

a substituted or unsubstituted 6 membered carbocyclic or heterocyclic aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-, pyridin-2-yl, pyridine-3-yl, pyridin-4-yl, pyrimidin-2-yl, pyrimidin-5-yl, pyrimidin-4-yl, pyridazin-3-yl, and pyridazine-4-yl; and a substituted or unsubstituted saturated heterocyclic group selected from piperidin-2-yl, piperidin-3-yl, piperidin-4-yl, tetrahydrofuran-2-yl, and tetrahydrofuran-3-yl, tetrahydropyran-2-yl, tetrahydropyran-3-yl, and tetrahydropyran-4-yl.

3. The compound according to claim 2, or a pharmaceutically acceptable salt thereof, wherein R$^{311}$ is selected from:

a substituted or unsubstituted linear or branched C$_1$-C$_6$ alkyl group selected from Me, Et, Pr, i-Pr, n-Bu, i-Bu, t-Bu, pentyl and hexyl;

a substituted or unsubstituted linear or branched C$_1$-C$_6$ alkyl-aryl group selected from —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph;

a substituted or unsubstituted cyclic C$_3$-C$_8$ alkyl group selected from cyclopropyl, cyclobutyl, cyclopentyl, cyclohexyl, cycloheptyl and cyclooctyl;

a substituted or unsubstituted aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-; and a saturated or unsaturated, substituted or unsubstituted, heterocyclic group selected from pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl.

4. The compound according to claim 1, or a pharmaceutically acceptable salt thereof, selected from one of the following:

4

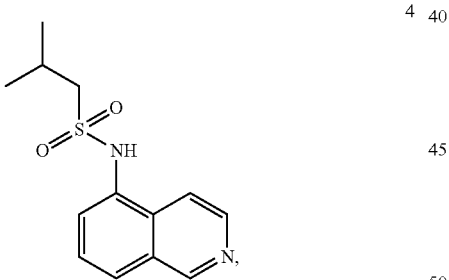

6

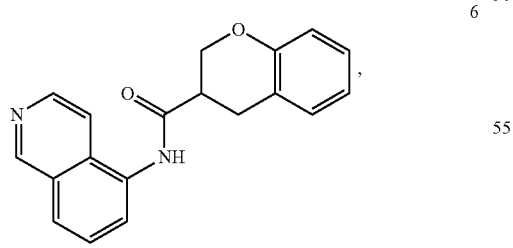

7

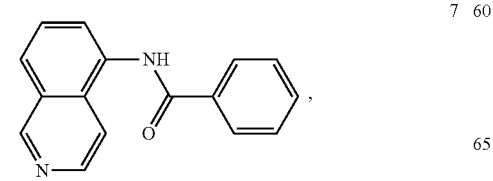

8

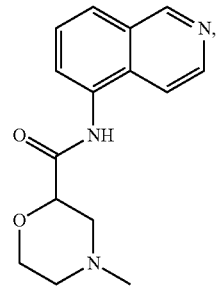

9

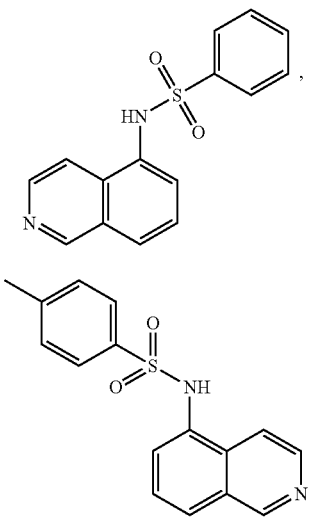

,

10

11

12

13

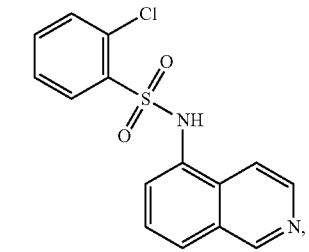

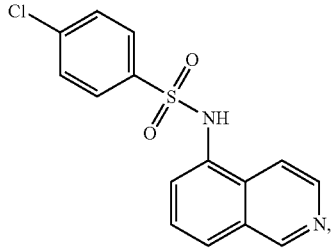

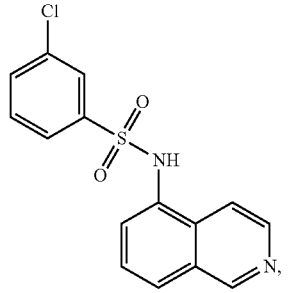

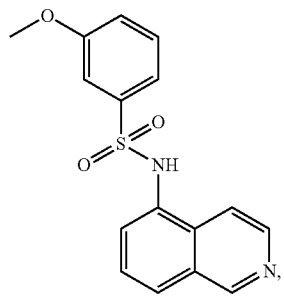
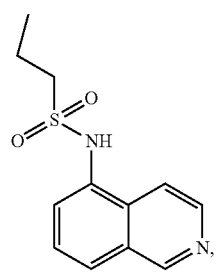
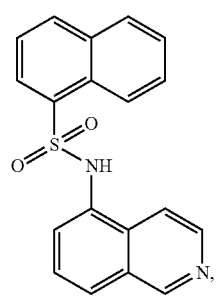
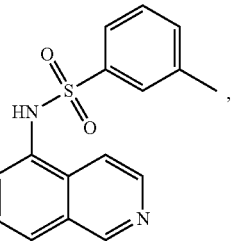
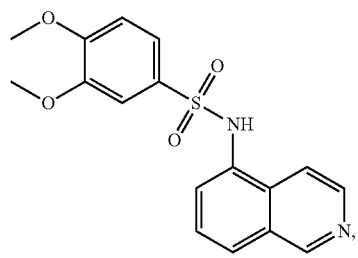
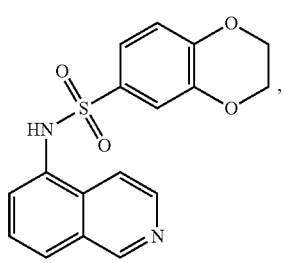
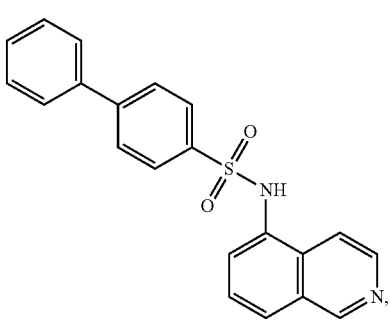
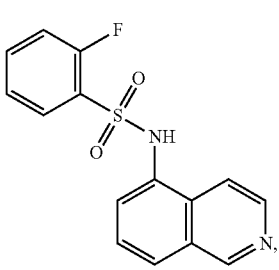
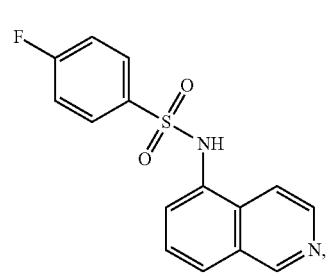
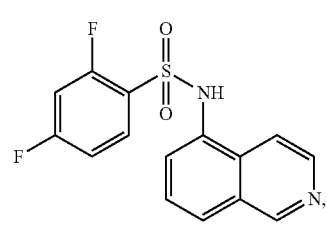
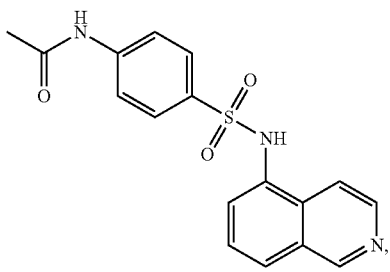
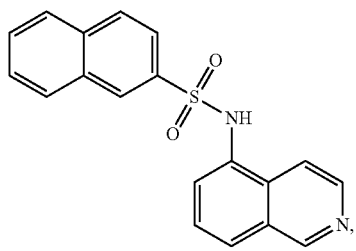

26
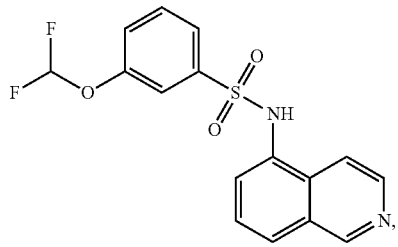
27
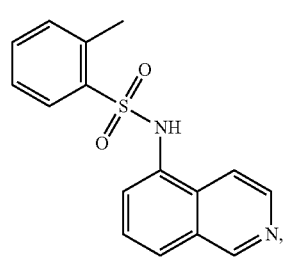
28
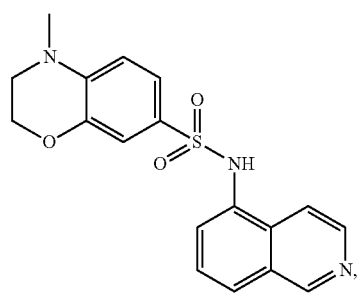
29
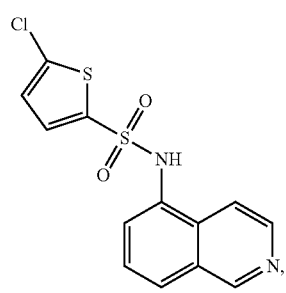
30
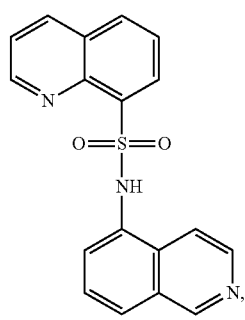
31
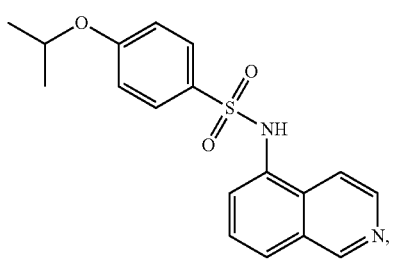
34
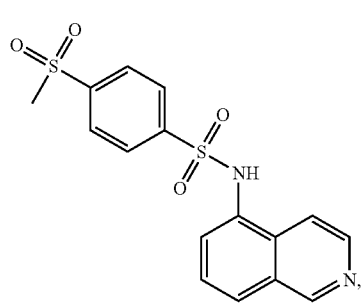
35
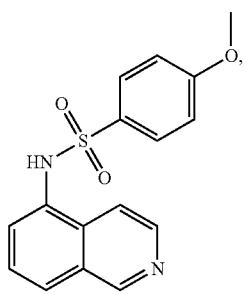
36
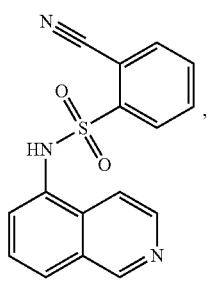
37
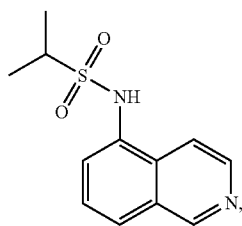

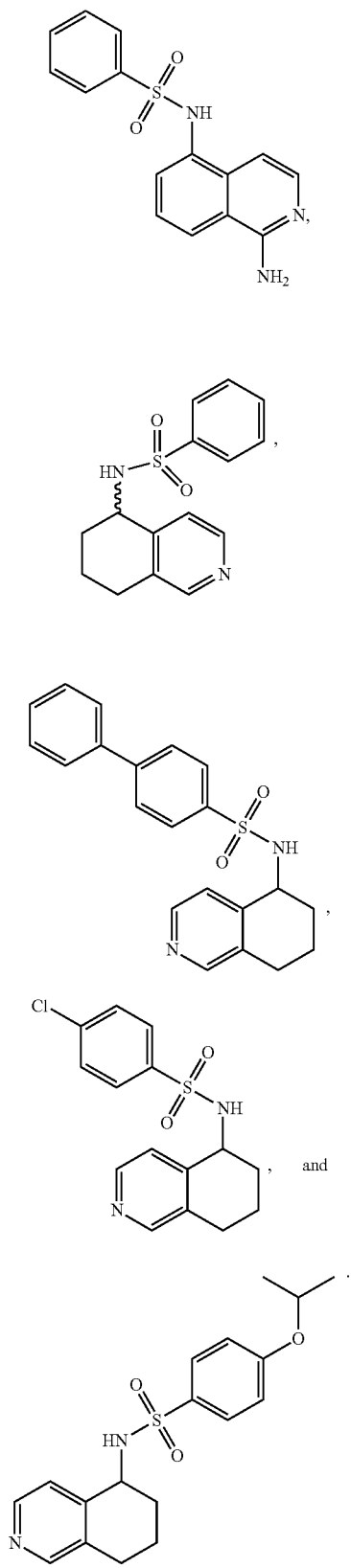
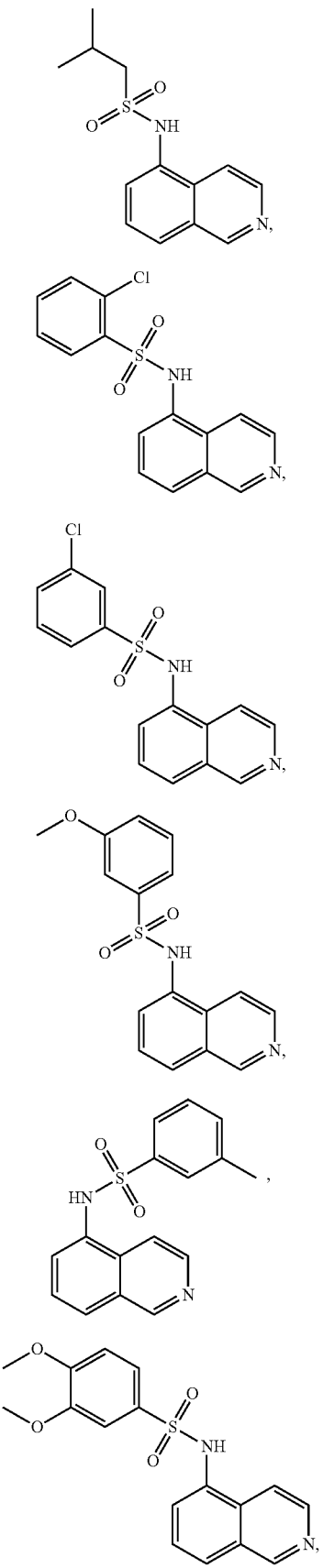
5. The compound of claim 1, selected from the following formulae, or a pharmaceutically acceptable salt thereof:

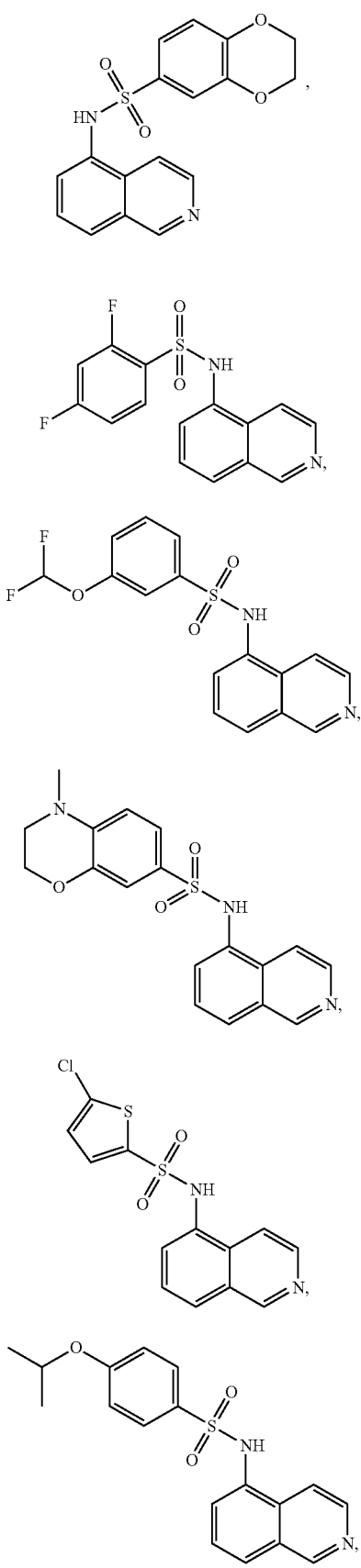
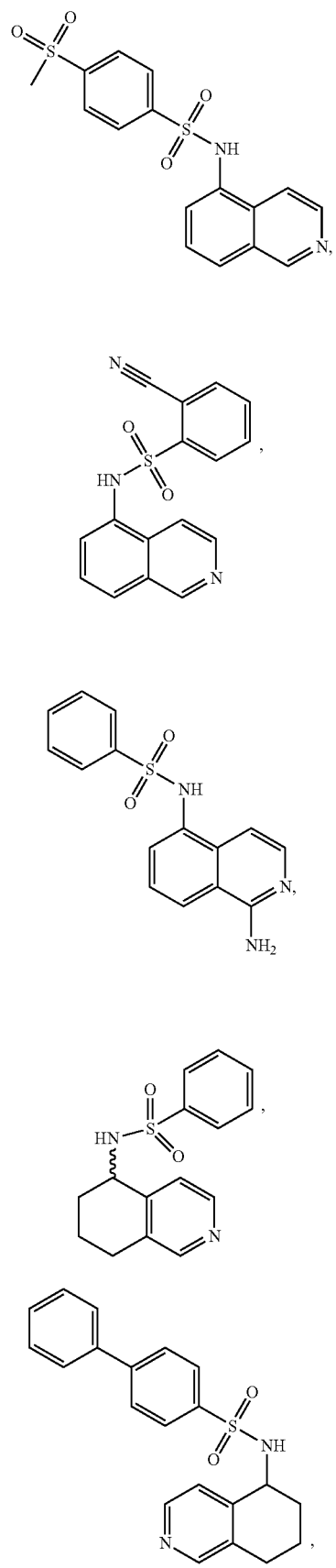

-continued
51
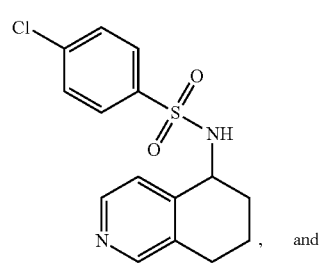
, and
52
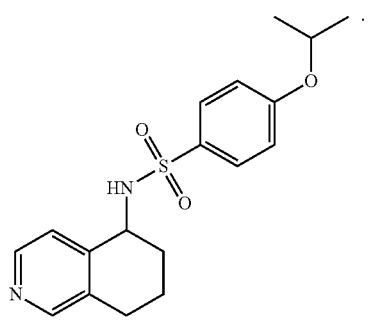
.
6. A pharmaceutical composition comprising a compound as defined in claim 1, or a pharmaceutically acceptable salt thereof, and a pharmaceutically acceptable additive and/or excipient.
* * * * *